United States Patent [19]

Frechet et al.

[11] Patent Number: 5,431,807
[45] Date of Patent: Jul. 11, 1995

[54] MULTIMODAL CHROMATOGRAPHIC SEPARATION MEDIA AND PROCESS FOR USING SAME

[75] Inventors: Jean M. J. Frechet; Frantisek Svec; Vladimir Smigol, all of Ithaca, N.Y.

[73] Assignee: Cornell Research Foundation, Inc., Ithaca, N.Y.

[21] Appl. No.: 212,155

[22] Filed: Mar. 14, 1994

Related U.S. Application Data

[62] Division of Ser. No. 964,404, Oct. 21, 1992, Pat. No. 5,316,680.

[51] Int. Cl.$^6$ ............................................. B01D 15/08
[52] U.S. Cl. .............................. 210/198.2; 210/502.1; 210/635; 210/656; 502/401; 502/402; 502/404
[58] Field of Search .................... 210/635, 656, 198.2, 210/502.1; 502/401, 402, 404; 530/413, 417

[56] References Cited

U.S. PATENT DOCUMENTS

| | | | |
|---|---|---|---|
| 4,000,098 | 12/1976 | Hofstee | 210/198.2 |
| 4,155,846 | 5/1979 | Novak | 210/198.2 |
| 4,160,728 | 7/1979 | Kirkland | 210/198.2 |
| 4,298,500 | 11/1981 | Abbott | 210/198.2 |
| 4,301,139 | 11/1981 | Feingers | 210/198.2 |
| 4,544,485 | 10/1985 | Pinkerton | 210/198.2 |
| 4,699,717 | 10/1987 | Riesner | 210/198.2 |
| 4,740,306 | 4/1988 | Litwack | 210/198.2 |
| 4,778,600 | 10/1988 | Williams | 210/198.2 |
| 4,810,391 | 3/1989 | Bruegger | 210/198.2 |
| 4,941,974 | 7/1990 | Williams | 210/198.2 |
| 4,950,635 | 8/1990 | Williams | 210/198.2 |
| 5,004,547 | 4/1991 | Grunfeld | 210/198.2 |
| 5,110,784 | 5/1992 | Williams | 210/198.2 |
| 5,130,343 | 7/1992 | Frechet | 521/62 |
| 5,133,868 | 7/1992 | Atwood | 210/198.2 |
| 5,137,627 | 8/1992 | Feibush | 210/198.2 |

OTHER PUBLICATIONS

Wheatly, "Multiple Ligand Applications in High-Performance Immunoaffinity Chromatography", Journal of Chromatography, 603 (1992) pp. 273–278.

Little, "Sequential Multimodal Elution for Pseudomultidimensional Liquid Chromatography on a Single Column," Anal. Chem., 63 (1991) pp. 33–44.

Pinkerton "High-Performance Liquid Chromatography Packing Materials for the Analysis of Small Molecules in Biological Matrices by Direct Injection", Journal of Chromatography, 544 (1991) pp. 13–23.

Haginaka, "Drug Determination in Serum by Liquid Chromatography with Restricted Access Stationary Phases", Trends in Analytical Chemistry, vol. 10, No. 1, 1991, pp. 17–22.

Flory, Principles of Polymer Chemistry, Cornell University Press, 1953, Ithaca, New York, pp. 266–269, 422–425, 594–597, & 606–607.

*Primary Examiner*—Ernest G. Therkorn
*Attorney, Agent, or Firm*—Bruce Jacobs

[57] ABSTRACT

A process for carrying out in a consecutive fashion different modes of chromatographic separation in a liquid chromatography column using a single separation medium is disclosed. Separation media for use in such multimodal separations are also disclosed.

30 Claims, 7 Drawing Sheets

MULTIMODAL CHROMATOGRAPHIC SEPARATION MEDIA AND PROCESS FOR USING SAME

This invention was made with government support under Grant No. GM44885-01 awarded by the National Institutes of Health. The government has certain rights in the invention.

This is a divisional of application Ser. No. 07/964,404 filed on Oct. 21, 1992, now U.S. Pat. No. 5,316,680.

BACKGROUND OF THE INVENTION

The art of liquid column chromatography is an old and well known means for separating a material from a sample. Depending upon the sample and materials to be separated therefrom, one of a variety of modes of liquid column chromatography is used to effect the separation. Such chromatographic modes include size exclusion (SEC), ion-exchange, reversed phase, normal phase, hydrophobic interaction, hydrophilic interaction, affinity, donor-acceptor, ion-pair and chiral separation chromatography.

Size-exclusion chromatography (SEC) generally comprises the differential elution of solutes from a bed of a porous chromatographic medium, caused by different degrees of steric exclusion of the solute molecules from the pore volume in pores with smaller size than is the size of the molecule to be eluted. The smaller the molecule, the more pores (the higher pore volume) of the porous separation medium (column packing) is available for their penetration. SEC is used in the separation of macromolecules according to their actual size defined by their hydrodynamic volume. Ideally, there is no interaction of any kind between the solute molecules and the chromatographic separation medium in SEC as the separation is driven by entropic changes.

In contrast to SEC, all other modes of liquid chromatography are based on an interaction between the compounds to be separated dissolved in a mobile phase and the stationary phase, i.e. the solid column packing which is why these modes are called interactive. The driving force of the separation is the difference in enthalpy of interactions of different compounds.

Classical column liquid adsorption chromatography, also referred to as normal or direct phase chromatography, is performed on a hydrophilic adsorbent such as silica and alumina with non-polar to moderately polar solvents. Normal phase chromatography has many drawbacks and the frequency of its use is declining.

Reversed phase chromatography (RPC) has been the most important branch of high-performance liquid chromatography (HPLC) since the early 1970s. The system for RPC consists of nonpolar (hydrophobic) stationary phase and a polar mobile phase. The primary interaction responsible for retention is essentially a solvent effect similar to the hydrophobic effect. Specifically, it is a noncovalent association of non-polar moieties in aqueous media. As the interactions depend on the type of molecules, they are the driving force for the separation. The typical mobile phases used in RPC are aqueous solutions of displacement agents, such as acetonitrile or 1-propanol. Elution with a mobile phase having constant composition (isocractic elution) is typically used in separations in low molecular weight compounds, while large molecules, like proteins, are eluted with a mobile phase in which the concentration of the displacement agent increases gradually (gradient elution).

Hydrophobic interaction chromatography (HIC) is an important separation mode for purification and separation of biomolecules. In this mode, hydrophobic ligands are chemically attached to hydrophilic matrix and a distinct interaction is obtained between biomolecules, such as proteins, and the stationary phase surface in the presence of high concentration of antichaotropic salt aqueous solution at neutral pH. Elution is achieved by diminishing the hydrophobic interaction by a descending salt gradient.

Hydrophilic interaction works in a similar manner as RPC except that the porous separation medium contains hydrophilic groups instead of hydrophobic groups.

Ion-exchange, in a broad sense, is the reversible interchange of ions of like charge between a solution and a solid, insoluble material in contact with it, the ion exchanger. All ion exchanges are reversible, but the equilibria for different ions under particular conditions vary widely, and it is these variations that make ion-exchange chromatography possible. The ion exchange is controlled by electrostatic interaction between the ions being exchanged, the mobile ions in a solution, and the fixed ions either acidic groups (carboxyl, sulfonate) or basic groups (tertiary and quaternary amines).

Ion chromatography is a separation of ionic species, typically low molecular weight anions or cations, on a column packed with a low capacity ion exchanger with detection by electrical conductivity. The ions to be separated are retained in the column according to the strength of their interaction with attached ion-exchange groups in very dilute eluent.

Ion-exchange chromatography is often used for separation of proteins and other large charged biopolymer molecules. The proteins are adsorbed into the separation medium at the beginning of the separation process in a mobile phase buffer with low ionic strength. The elution of individual components of the separated mixture is achieved with an increasing salt concentration gradient in the mobile phase.

An alternative to ion-exchange chromatography for analysis of organic anions, like those of alkaloids, peptides, or surfactants, is ion-pair chromatography. The anions combine with a cationic surfactant, such as cetyltrimethylammonium bromide, to form hydrophobic complexes which are separated in a standard reversed phase chromatography.

Ligand-exchange chromatography depends on the exchange of electron-donor ligand around a central metal ion loaded in a special cation exchanger. The metal ion does not move while the ligand(s) coordinated to it is exchanged according to its complex building ability. The most exciting application of ion-exchange chromatography is the separation of optical isomers of amino acids. The chiral resolving ligand, such as L-proline, is attached to the stationary phase and a copper complex is made. The D-form of the amino acid binds more tightly to the solid phase while the L-form is eluted already with water and very good separation is achieved.

Separation of chiral molecules based on enantioselective adsorption may also be achieved upon another mechanism other than ligand exchange. The chiral recognition and the retention is controlled by hydrogen binding, $\pi$-$\pi$ interaction. The separation medium plays a very important role in chiral separation chromatography and it has to be perfectly designed to contain at least three points of interaction between chiral separation phase and analyte molecule, at least two of which should be attractive.

The application of the donor-acceptor complex formation results in the donor-acceptor complex chromatography (DACC). A donor or an acceptor is chemically bonded to the surface of an insoluble porous matrix and separates solutes possessing acceptor or donor properties, respectively. Typical electron acceptor phases contain attached dinitroanilinoalkyl groups while the typical electron donor phase is featured by pentamethylphenyl or phenanthryl groups. The mobile phase is non-polar but, surprisingly, the media work in the polar mobile phase as well. The major application area of DAAC is separation of unsaturated organic compounds, chlorinated aromatic coumpounds, amino acids, on one hand, and polynitro-substituted aromatic compounds and similar derivatives, on the other. DAAC approach is also useful for the separation of enantiomers.

Affinity chromatography incorporates a large family of adsorption chromatography methods, all of which utilize more or less specific interaction between biological molecules in solution and covalently attached ligand molecules on a solid phase. In addition to classical biospecific affinity chromatography, the methods are charge-transfer affinity chromatography (similar to DACC), immobilized metal affinity chromatography (similar to ligand exchange chromatography), dye ligand affinity chromatography, immunoaffinity chromatography (immunosorption), and covalent chromatography (chemisorption). The names specify usually the immobilized ligand or type of interaction. The higher the specificity of the solute-sorbent interaction, the closer the separation process amounts to "fishing out" the particular biological molecule, and the further the process is from the typical chromatographic separation. The most specific immuno-affinity chromatography based on interaction with an immobilized antibody results in the capture of one single antigen dissolved in the mobile phase without requiring the separation of all other components of the sample. After saturation of the column capacity with the soluble antigen, the adsorbed column is washed free of any contaminant compounds and the antigen is displaced from the solid phase of the separation medium. The separation may be repeated again after re-equilibration of the column.

Each of these chromatographic modes is particularly useful for separations of specific groups of compounds. The separation media are specially designed for a particular chromatographic mode and usually do not work in another mode adequately.

The problem with such specific separation techniques is that often a liquid sample contains a variety of molecules which require different modes of separation. This, however, is not easily accomplished because different modes of separations usually require different separation media to effect the separation of different molecules. This requires the use of multiple columns and multiple separation media to accomplish the desired separations.

It may be possible to use combinations of different separation media in different columns for multimodal separations. An example of this multiple column bimodal separation was described recently by Wheatley J. B., *J. Chromatogr.*, 603 (1992) 273. The bimodal separation of small molecules in one column packed with one separation medium and based on sequential multimodal elution was described by Little E. L., Jeansonne M. S., Foley J. P.; *Anal Chem.*, 63, 1991, 33. They combined ion-exchange and reversed phase chromatography for the separation of a complex sample containing two groups of compounds: charged and non-polar. The use of two different gradients, i.e. a pH gradient and a methanol gradient, resulted in the separation of the charged molecules first, followed by the separation of the neutral molecules after switching to the second mobile phase. This approach makes use of imperfect surface functionalization of porous silica beads which contained $C_1$, $C_8$ or $C_{18}$ groups together with the original acidic surface silanol groups. Similarly, the DIONEX OmniPack PAX-500 column is packed with non-porous poly[styrene-divinylbenzene] beads coated on the bead surface with attached ion-exchange latex particles (as described by the DIONEX booklet). Here again, the coating of the bead surface is imperfect and it is the non-covered hydrophobic areas of the original non-porous beads that are used for separation in the second mode. This approach excludes combinations not involving the reversed phase mode (the original ST-DVB surface remains non-polar even after attachment of latex particles) as well as any size exclusion separation.

These prior bimodal separations fail when used with a large number of biological samples where biopolymers, like proteins or nucleic acids, are present along with small molecules, such as drugs, metabolites, pollutants, exo- and endotoxins, etc. Since sample pretreatment, like solvent extraction, solid phase extraction or ultrafiltration, is time-consuming and tedious, new stationary phases have been developed which prevent contact between the groups used for separation in the reversed phase or ion-exchange chromatography. Media that have very small pores preventing large molecules from penetration into the bead (total exclusion), are mostly used. Clogging of the column by proteins stuck on the bead surface is inhibited by providing the surface with hydrophilic groups. This approach was reviewed recently (Pinkerton T. C., *J. Chromatogr.*, 544, (1991) 13; Haginaka J., *Trends Anal. Chem.*, 10, (1991) 17). It may be called pseudomultimodal as one of the modes is actually not a chromatography but a simple filtration-like separation (total exclusion of all molecules exceeding a size limit). The separation of individual components of the excluded part of the sample, however, requires an additional column. Moreover, such bimodal separation as disclosed by Foley et al and Dionex are not generally useful but rather are applicable solely to the specific modes of separation disclosed.

It would be a substantial advantage to develop a process which could use different combinations of the various modes of chromatographic separation depending upon the molecules to be separated without changing the separation medium within the column or using different columns. Such a process would be more economical and time efficient.

SUMMARY OF THE INVENTION

Accordingly, the present invention is directed to a process for separating molecules from a sample containing at least two different molecules comprising (1) adding the sample to a chromatographic column containing a single separation medium, said separation medium comprising a porous material having pores of at least two different size ranges with each size range pore containing different surface groups having a different functionality compared to the surface groups in the other size range pores, (2) using the different surface groups within the different size pores to separate the different molecules from each other and the sample, said separation being carried out using at least 2 and up to about 5, but more preferably 2 to 3, modes of separation in a consecutive manner using the same separation medium, so as to separate during each mode of chromatographic separation different molecules from the sample.

This multimodal separation process is able to achieve separation in a single column in a consecutive operation because of the properties of the separation medium. The separation medium generally comprises a porous material which has been pretreated so that it has at least two different types of surface groups which have different functionalities. These different surface groups are disposed in different size range pores within the porous material. Pore size as used herein can mean a single measured average size, for example, 25 nm, but in most cases it means a particular range of sizes, for example, 50–500 nm. An example of such a porous material of the present invention is one wherein there are hydrophilic surface groups in pores having a size of from about 5–25 nm and hydrophobic surface groups in pores ranging in a size of from about 30–50 nm. Another example is a material having hydrophilic groups in pores below 25 nm in size and hydrophobic groups in pores above 25–30 nm in size. As a result of the different functionalities of the surface groups, molecules that have affinities to such different surface groups may be separated during different modes of separation, which may be carried out in a consecutive fashion. As used herein, different molecules means molecules of different sizes, different chemical affinities, different structures, compositions, polarities, chiralities, activities, etc.

The different molecules are separated during the process of the present invention by using a mobile phase having a particular composition which may be varied depending upon the mode of separation being used. The mobile phase composition can be changed either in steps or in a continuous manner by changing the type of the solvent and the concentration of the displacement agent, such as strong eluent, inorganic salt, chaotropic compound, and the like, in the liquid mobile phase. The mobile phase may change completely when switching from one chromatographic mode to another while the displacement agent in the particular mobile phase may remain the same during the chromatographic mode or it may be changed in steps or continuously (displacement agent gradient) in each mode.

The following terms shall have the indicated definitions unless otherwise indicated:

"Mobile phase" is a liquid that moves dissolved components of a mixture that is to be separated through a chromatographic column. The mobile phase very often contains more than one compound and is a mixture of different solvents or a solution of salts, acids, bases, etc.

"Solvent" is a liquid single chemical compound.

"Eluent" is a mobile phase used to carry out a separation.

"Displacement agent" is a a compound that is more strongly sorbed than the compounds of the original mixture and displaces them from the column. (see Modifier)

"Mobile phase strength" refers to the strength of the mobile phase in terms of, e.g., polarity, organic modifier concentration in reversed phase chromatography, buffer ionic strength in ion-exchange chromatography or hydrophobic interaction chromatography.

"Modifier" is an additive that changes the character of the mobile phase. (see Displacement agent)

"Gradient" is a change in the composition of a mobile phase with time.

DETAILED DESCRIPTION OF THE INVENTION

Figure 1A:
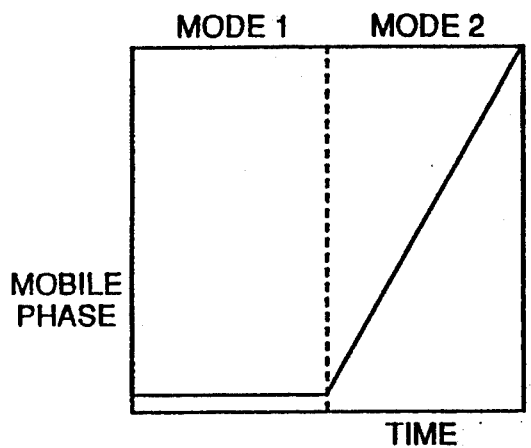
FIGS. 1–10 are graphical representations of the results of the separations carried out in Examples 1–8.
Figure 1B:
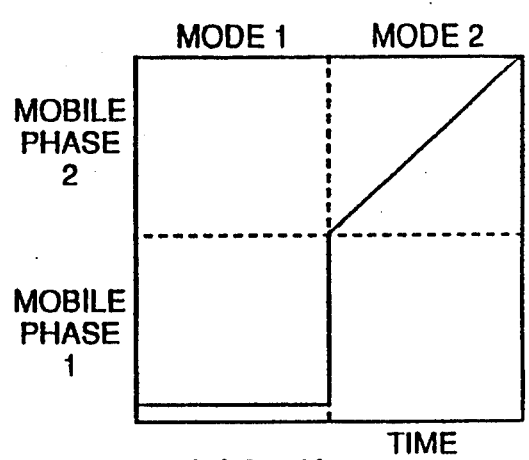
Figure 1C:
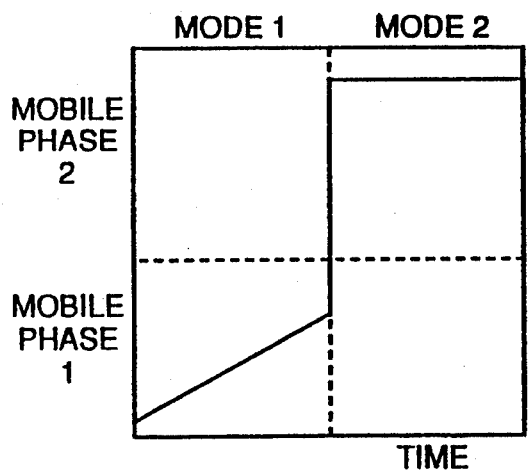
Figure 1D:
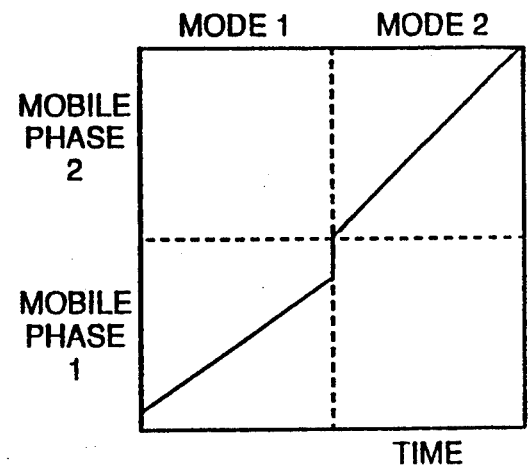
Figure 1E:
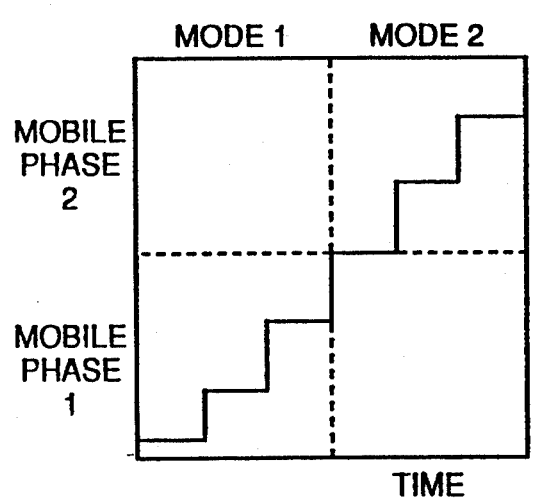

More particularly, the process of the present invention for separating different molecules from a sample containing such molecules comprises passing a liquid sample containing at least two different molecules through a liquid chromatography column. Any suitable column may be used. The column is made of standard materials such as stainless steel, titanium, glass, silica, and poly(ether ether ketone) or any other inert polymeric material. The size of the column depends on the scale of separation. Typically, the columns have sizes such as $100 \times 4$ mm i.d., $150 \times 4$ mm i.d., $250 \times 8$ mm i.d., etc., for analytical separation while the size of the column is considerably larger for preparative separations. There is, however, no limit in the column size in the process of the present invention. The liquid sample is passed through a separation medium packed within the column by standard techniques. The separation medium, as will be explained in greater detail hereinafter, contains pores of at least two different sizes, with each size pore containing different surface groups with different functionalities.

The process is carried out using one mode of separation such as any of size exclusion, ion-exchange, reversed-phase, normal phase, liquid-exchange, hydrophobic interaction, hydrophilic interaction, affinity, donor-acceptor, ion-pair and chiral separation chromatography, and then continued using a different mode of separation. The modes of separation are carried out in a consecutive fashion, in the same column using the same separation medium. The process of the present invention may be carried out using at least 2 or more modes of separation and up to as many as about 4 such modes. The number of separation modes in a single medium is only limited by the pore size distribution of the medium and the availability of reagents and/or catalysts with sufficiently different molecular sizes. More preferably either 2 (bimodal) or 3 (trimodal) chromatographic modes of separation will be used with a single medium. The process is particularly suitable for running 2 and 3 modes of separation in a consecutive fashion.

Any of the chromatographic modes of separation including all of those described herein may be combined together. For example, an exclusion mode, such as SEC, may be used with two or more interactive modes, e.g. ion-exchange, reversed phase, etc., or two or more interactive modes may be used consecutively.

Particularly preferred bimodal separation processes include size-exclusion chromatography (SEC) combined with reversed phase, ion exchange combined with reversed phase, SEC combined with reversed phase, hydrophobic interaction combined with reversed phase. Particularly preferred trimodal separation processes include SEC combined with ion-exchange and reversed phase chromatography, SEC combined with affinity and reversed phase chromatography, and affinity chromatography combined with ion-exchange and reversed phase chromatography. While any mode may be combined with any other mode of separation, each combination requires different chromatographic conditions such as the mobile phase composition and gradients. These different conditions can be designed based on the separation medium and the molecules to be separated.

For example, SEC does not need any specific surface groups to interact with, but rather is based on the absence of any interaction. Therefore, SEC can be performed in any medium provided there is no interaction with the surface groups. Thus, if SEC is used to separate large molecules as the first mode of separation, a mobile phase must be used which does not prevent interactions of the relatively small molecules in the sample with the surface groups in the smaller pores in the separation medium. Similar interactions with the large molecules are avoided in choosing the separation medium. For example, if molecules to be separated from a sample are hydrophobic drugs and polymers such as poly(ethylene oxides), the mobile phase should be designed in the same way as for gradient reversed phase chromatography. Such a mobile phase will typically contain water as a major component until the SEC separation of polymeric molecules is finished and then replaced by a modified aqueous mobile phase containing a constant concentration of acetonitrile (modifier). The gradient is a two-step gradient supporting two isocratic elutions. The interaction of polymer molecules does not take place with the surfaces in the pores that are available to them while the small, low molecular weight hydrophobic compounds are firmly absorbed on the surface groups on the relatively small pores of the separation medium. SEC separation will occur at the beginning of the process followed by reversed phase separation after the addition of a displacement agent such as acetonitrile or propanol.

A combination of SEC (larger pores) and ion-exchange chromatography (smaller pores) separation modes would work similarly. A sample containing, for example, proteins and weak organic acids is injected in an aqueous mobile phase containing very low constant concentration of inorganic salts (low concentration phosphate buffer solution, e.g. 0.01 mol/l). The proteins will be separated in the relatively large pores according to their hydrodynamic size while the acids will be retained due to interaction with positively charged amino groups in relatively small pores. They will be separated after the ionic strength of the mobile phase, changed in an increasing concentration gradient of sodium chloride, will reach the point at which the retained molecules will start to move.

Different conditions have to be chosen for combinations of hydrophobic interaction (larger pores) and reversed phase chromatography (smaller pores). A sample containing proteins and low molecular hydrophobic drugs will be injected in an aqueous mobile phase which contains a relatively high concentration of an inorganic salt, typically 2 mol/l sodium chloride. For the separation of proteins, the concentration of salt needs to decrease in a descending linear gradient. Proteins will be released consecutively from the column while the strength of the mobile phase will not be sufficient to break the interaction of highly hydrophobic groups in smaller pores with the low molecular weight drugs. They will be separated only after a solvent such as acetonitrile or propanol will be added to the mobile phase.

The key in selecting a mobile phase for a multimodal separation is the consecutive use of mobile phases, in each individual mode, that do not interfere with the absorption of compounds to be separated in any of the subsequent modes. Otherwise, the separation will not be multimodal and one group of compounds will leave the column without any separation, as documented in Example 6 and FIG. 7. Under this assumption, even a mobile phase for trimodal separation is easily designed by a person skilled in the art of liquid chromatography.

For example, if a sample containing proteins and weak organic acids have to be separated in three consecutive modes, SEC (large pores), reversed phase (medium sized pores) and ion-exchange chromatography (smaller pores), the first mobile phase used for separation of large proteins in SEC mode will be a simple buffer solution (0.01 mol/l phosphate buffer). Proteins with a molecular weight between 10,000 and 20,000 will be absorbed in medium sized pores by a strong hydrophobic interaction while the acids will move to the smaller pores and interact with amino groups located therein. After all large proteins are eluted, an increasing gradient of acetonitrile or propanol will start the separation of the small proteins without affecting the ion-ion interactions in the small pores. The last groups of compounds located in the smaller pores will be separated using an increasing gradient of inorganic salt concentration in the original buffer. It follows from this description that there will be no difference in separation when the last two modes (reversed phase and ion-exchange) are interchanged in time as the salt does not influence the reversed phase mode and the solvent modifier does not interfere with the ion-ion interactions.

To obtain better separations with less restricted diffusion in the pores, it is currently recommended that the mobile phase be designed in such a manner as to separate the molecules according to their location in the pores of the medium starting with the largest pores and going down to the smallest pores. This approach also implicitly includes the requirement that the SEC mode, if used, be the first mode of chromatography. Then, proteins are separated first by using a mobile phase comprising diluted buffer solution while the other molecules are retained on the medium and separated in a following step after an organic solvent is added to the mobile phase. This approach results in a chromatogram with two clearly separated domains or peaks. When, instead, a separation of a sample comprising proteins and small hydrophobic molecules starts with a mobile phase containing an organic solvent, both proteins and small molecules are eluted together and the peak capacity of the separation medium decreases considerably. Both modes (SEC and reversed phase chromatography) will run in parallel and the separation will be insufficient. The resulting chromatogram will be an overlay of two independent separations. Data interpretation would be more difficult, though the use of two detectors working on different principles (or a dual-purpose detector) and a computerized deconvolution may help to solve the problem.

In conjunction with the mobile phase and in order to make the process work, the separation medium must be designed for the particular separation desired. Thus, if size exclusion is desired, the separation medium must be selected so as to have pores distributed over the necessary range of sizes covering the molecular volumes of the macromolecules to be separated. In the normal phase, the surface is provided with polar groups while for the reversed phase the surface must be hydrophobic. In the case of hydrophobic interaction, the separation medium must be designed to have hydrophobic groups attached to a hydrophilic surface. If ion exchange is one of the modes desired, ion-exchange functionality must be possessed by at least some groups located within pores of the separation media. For ligand exchange some metal ions have to be complexed by selected groups in defined pores. The chiral separation, donor-acceptor complex and affinity chromatographic modes call for chiral selector groups, donor groups, acceptor groups and immobilized ligand, respectively, attached in preselected pores.

Determination of different functionalities of the porous material represents routine work for those skilled in the art and will depend upon the type of functionality to be determined. Typical means of chemical and instrumental analysis can be used. For example, elemental analysis of nitrogen in separation medium can reveal the content of amino or nitro groups; an acid-base titration can determine the acidic or basic groups; the content of epoxide, benzylidene or other groups can be determined by means of standard spectroscopic techniques.

A large variety of porous separation media may be employed in the process of the present invention. Suitable porous materials include macroporous polymers such as polymers of glycidyl methacrylate or acrylate; 2-hydroxyethyl methacrylate or acrylate; allyl methacrylate or acrylate; chloromethylstyrene; 4-t-butoxycarbonyloxystyrene; vinylacetate; vinylacetals; vinyl alcohol, vinylbenzyl alcohol, or vinyl phenol and esters or ethers thereof; 4-nitrophenyl acrylate; 2,4,5-trichlorophenyl acrylate; acryloyl succinimide; maleic acid; vinylbenzaldehyde, acrolein, or methacrolein or acetal, imine, oxime, or hydrazone derivatives thereof; crosslinked with any of divinylbenzene; ethylene dimethacrylate or acrylate; diethylene glycol methacrylate or acrylate; divinylpyridine; bis-N-vinyl-2-pyrrolidone; N,N-methylene-bis-acrylamide;ortrimethylolpropanetrimethacrylate. Other suitable porous materials are those based on natural polysaccharides such as cellulose, chitin, agarose, guar, mannan, and dextran. The porous material may also be an inorganic oxide such as silica, titania, zirconia, alumina, magnesia, and porous glass. Other suitable porous materials include a bonded reactive phase materials prepared by the reaction of an inorganic oxide with a reactive silylation agent such as 1-glycidoxypropyl-trimethoxysilane, and vinyltrimethoxysilane.

The medium pore size of the porous materials is generally from about 2 nm to 200 nm with the pore size distribution generally ranging from about 1 to 1500 nm. The pore size distribution is particularly important when SEC is employed. In such cases, pores of greater than about 2 nm are preferred. Standard porous materials are either commercially available from sources such as Showa Denko, Toyo Soda and Supelco, Bio-Rad, Rohm and Haas, and Pharmacia, or may be prepared by techniques known in the art such as disclosed in U.S. Pat. No. 5,130,343. The shape and size of the separation media may vary and can include irregular particles, beads, membranes, rods and rod-like shapes.

Each porous material contains particular reactive groups within its pores. Depending upon the porous material, the reactive groups can include groups such as epoxy, acetal, hydroxy, carbonyl, ester, chloromethyl, carboxylic acid and anhydride, imine, enamine, oxime, and hydrazone. The surface functionality resulting from each reactive group will vary among a large number of possibilities depending mainly on the reaction scheme selected and, to a lesser extent, on the initial reactive group. As can be seen in Reaction Schemes 1-5 below, initially an epoxide group is provided in each but the final functionalities are chemically very different. The reactive groups will determine which modifying agents need to be used to modify the reactive groups to obtain the desired surface functionality of the pores in the porous material.

The modifying agents are selected by their size and ability to react with or catalyze the modification of reactive groups in the pores of the porous material. The size of the modifying agent will be selected based on the pore sizes of the porous material containing reactive groups to be modified. The actual size of a modifying polymeric agent will depend upon the molecular weight of the polymer and on the solvent in which the reaction proceeds. (P. J. Flory, *Principles of Polymer Chemistry*, Cornell University Press, 1953, Ithaca, N.Y.) Suitable modifying agents may have molecular weights ranging from about 17 to more than one million and include such as polymeric catalysts such as poly(styrenesulfonic acid), poly(methacrylic acid), poly(acrylic acid), poly(vinylbenzoic acid), or a peracid thereof; poly(ethyleneimine) and its quaternized derivatives, poly(triethylaminoethyl methacrylate), polyvinylpyridine and its quaternized derivatives, or poly(trimethylaminomethylstyrene) and polymeric reagents including a polymeric carbodiimide or similar polymeric coupling agent; a polymeric dimethylaminopyridine or similar acylation agent.

In the case of the reagent, the reagent reacts with the reactive groups in the pores of the porous material into which it enters to change them chemically into different surface groups. The catalyst on the other hand functions by catalyzing the reaction of the reactive groups with a reagent present in the pores. For example, if the surface of the pores contains reactive epoxy groups and if the catalyst is a polymeric acid in water, the epoxy groups will react with water in a hydrolysis reaction that will transform the epoxy groups into diol groups only when the catalyst is present. In the areas where the polymeric acid catalyst is not present (small pores because of size constraints), the epoxy groups will not react with water since the hydrolysis reaction cannot occur in the absence of the catalyst. After the modification of desired pores is finished, the catalyst is washed out of the pores and may be reused for the next modification.

A few particular process schemes for making the porous material which forms the separation medium of the present invention are described hereinafter. Though numerous other reaction schemes are possible, the following schemes are shown to illustrate the basic concepts of the present invention. Other reactions and specific examples are contained in the Examples hereinafter.

In Reaction Scheme 1 and in Reaction Scheme 2 below, a porous material is derived from a copolymer composition containing

REACTION SCHEME 1

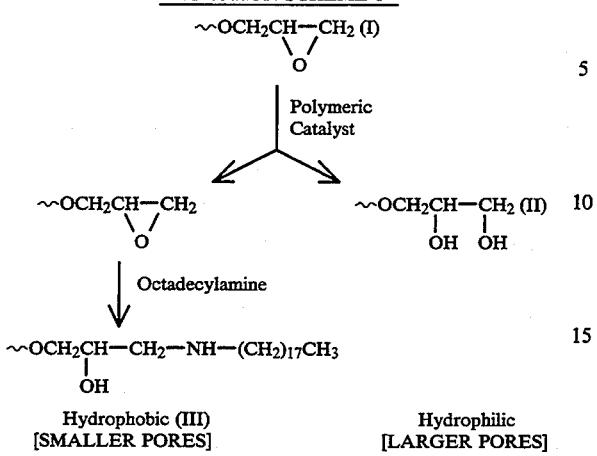

Hydrophobic (III)　　　　　　Hydrophilic
[SMALLER PORES]　　　　　[LARGER PORES]

glycidyl methacrylate. Therefore, the reactive groups are epoxides. Other suitable porous materials such as γ-glycidoxypropyl-trimethoxysilane activated porous silica beads may be used. The functionality of the surface groups rather than the particular porous material is more important to how the porous material functions as separation medium. In the reaction, a catalyst containing strongly acidic sulfonic groups is used together with water as a reagent to transform the hydrophobic epoxy groups (I) to diol groups (II) which are hydrophilic.

A polymeric catalyst such as poly(styrenesulfonic acid) containing strongly acidic groups, having a molecular weight of over one million may be used as the modifying agent. The polymeric acid used for the modification is unable to penetrate the pores having a size smaller than its molecular size in water. When the hydrolysis is catalyzed with such a polymeric catalyst, the epoxide groups present in pores inaccessible to such a catalyst (relatively small pores) remain unchanged and may be used in further step for other reactions.

If desired, the hydrophobicity of the pores containing remaining epoxy groups can be increased, for example, by a reaction with relatively small molecules such as higher alkylamines such as octadecylamine or dialkylamines with alkyls containing at least 8 carbon atoms, alkylarylamines or arylamines. The hydrophobicity of the long alkyl chain or aryl group in product III dominates over the polarity of the amino group. Such a product would be useful as a bimodal separation medium wherein the separation modes are SEC and the other mode is reversed phase.

On the other hand, reaction with an amine containing only short alkyl chains such as reaction with diethylamine shown in Reaction Scheme 2 results in product IV with pronounced anion-exchange surface functionality. The aminolyzed product is useful as a bimodal separation medium combining SEC and ion-exchange modes.

In Reaction Scheme 3, the porous material based on glycidyl methacrylate is again hydrolyzed in presence of aqueous sulfuric acid and the diol groups (ii) are reacted with benzaldehyde in the presence of sulfuric acid under anhydrous conditions to produce benzylidene acetal groups. The next step is hydrolysis of some of the benzylidene acetal groups catalyzed by a polymeric catalyst. The acetal groups in pores smaller than the size of the catalyst molecule remain unchanged while the others are transformed to a diol making the larger pores hydrophilic. This material already represents a bimodal separation medium for liquid chromatography including size exclusion and reversed phase.

REACTION SCHEME 2

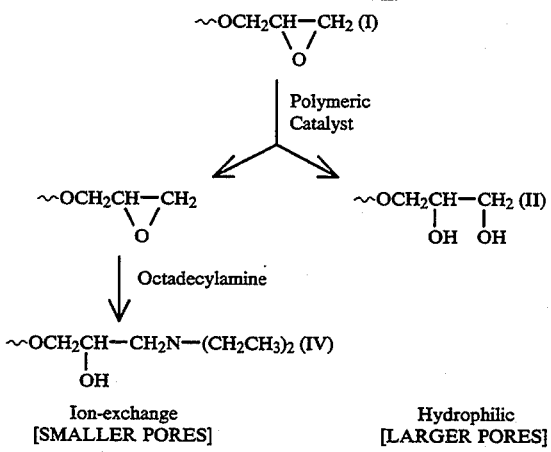

Ion-exchange　　　　　　　Hydrophilic
[SMALLER PORES]　　　　　[LARGER PORES]

Finally, the hydroxyl groups in large pores react with chloroacetic acid in aqueous sodium hydroxide producing charged cation exchange groups (VI). The net result is that the smaller pores contain hydrophobic benzylidene acetal groups (V) and the larger pores contain cation exchange groups. These porous beads would be useful as a bimodal separation medium in liquid chromatography wherein the separation mode is ion-exchange and the other mode is reversed phase.

REACTION SCHEME 3

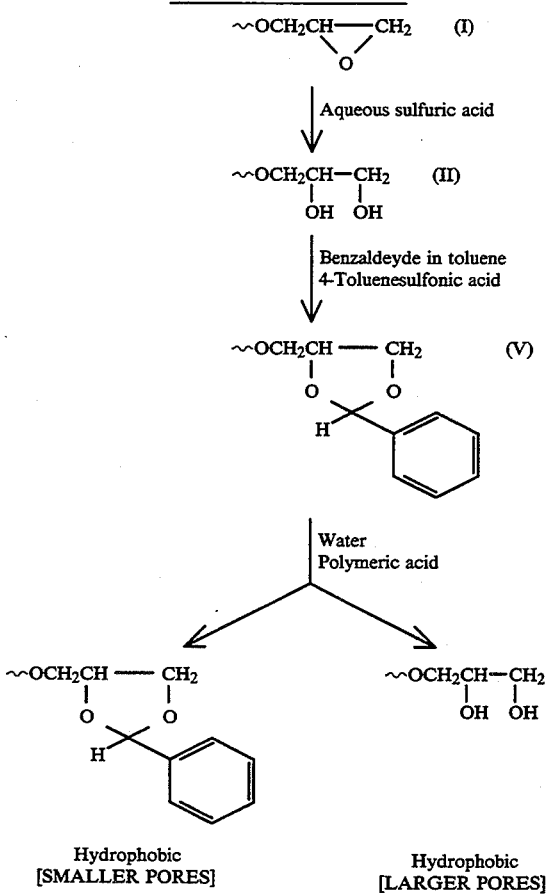

Hydrophobic　　　　　　　Hydrophobic
[SMALLER PORES]　　　　　[LARGER PORES]

-continued
REACTION SCHEME 3

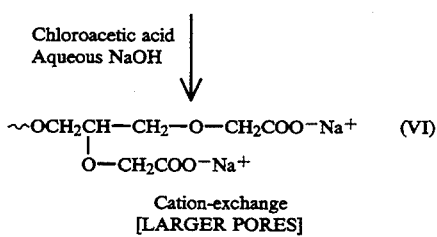

Cation-exchange
[LARGER PORES]

REACTION SCHEME 4

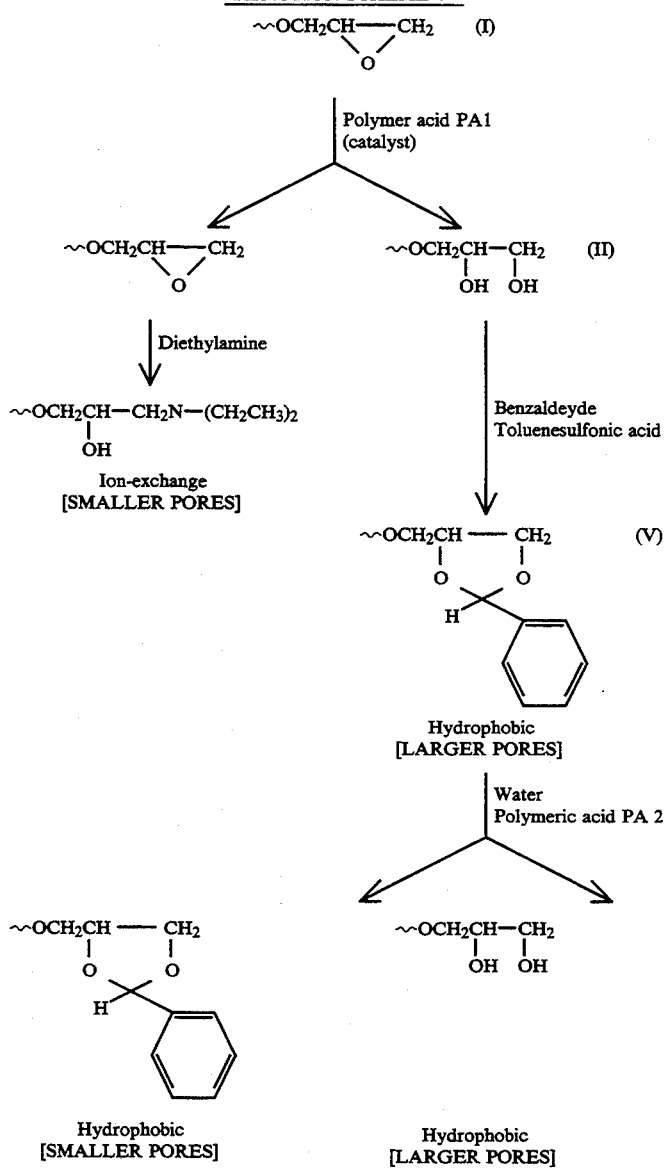

under catalysis of a low molecular weight acid in the absence of water which changes all the diol groups present in the relatively large pores to hydrophobic benzylidene acetal groups. The beads may be used as a bimodal separation medium in high performance liquid chromatography wherein the separation modes equal those of the bimodal separation medium described in Reaction Scheme 3 except for localization of the groups in pores of opposite size range.

Further treatment of the modified porous material with a polymeric acid in presence of water causes hydrolysis of benzylidene acetal groups V to original vicinal diol groups. Assuming that the polymeric acidic catalyst PA 1 used in the first modification reaction has molecular volume smaller than polymeric acid PA 2 used for hydrolysis of the benzylidene acetals ($M_{PA\ 1} < M_{PA\ 2}$), the acetal groups located in medium sized pores will survive the treatment and a material arises which has three different zones, i.e., small pores aminated for ion-exchange, medium pores hydrophobic, In Reaction Scheme 4, the starting porous material is again a copolymer of glycidyl methacrylate. Similar to Reaction Schemes 1 and 2, a polymeric catalyst is used as the catalyst in the first reaction step which causes hydrolysis of all epoxide groups unless they are hidden in the smaller pores inaccessible to the polymeric catalyst. The remaining epoxide groups in the small pores react with diethylamine producing ion-exchange groups. The product is then treated with benzaldehyde and large pores hydrophilic. The beads modified in a way described in the entire Reaction Scheme 4 are useful for a trimodal separation wherein the separation modes are size exclusion, reversed phase, and ion-exchange.

Reaction Schemes 1–4 not only describe the particular sets of reactions leading to multimodal separation media but they also show the concepts of making such media in general. The starting polymer must be porous with relatively broad pore size distribution and possess reactive groups on the surface of the pores. Typically, the pore-size selectivity of the modification reactions are controlled by the molecular weight of the catalyst or reagent used in the particular modifying reaction and by the solvent. The number of modes accommodated in a separation medium is theoretically not limited but practically will rarely exceed three. The most important part in designing the reaction strategy for preparation of a multimodal medium is the right choice of the path. The product of a given reaction affecting pores of a given size should not affect the groups already built up in the previous reaction step within pores of a different size.

The multimodal separation process of the present invention may even use very tiny differences between the separation modes as is the case with reversed phase and hydrophobic interaction chromatography. The separation medium can be prepared by a set of reactions shown in Reaction Scheme 5.

The first reaction of the original epoxide groups with phenol results in the attachment of a low amount of phenyl groups (VII) to the entire inner surface of the beads and makes it more hydrophobic. The second reaction with epichlorohydrin involves all the new surface reactive groups and gives second generation epoxy groups, VIII. The second generation epoxide groups in the large pores are hydrolyzed upon catalysis by polymeric acid. The modification increases the hydrophilicity of the larger pores which still contain some hydrophobic moieties and can be employed in the hydrophobic interaction chromatographic mode. The unreacted second generation epoxides in smaller pores which survive the action of polymeric catalyst react eventually again with phenol (IX) to increase the hydrophobicity. It makes them hydrophobic enough for their use for reversed phase separation.

The hydrophobic interaction mode is a very mild separation mode, similar to the ion-exchange chromatography, in which the activity of the protein is not destroyed. Here again, the separation

REACTION SCHEME 5

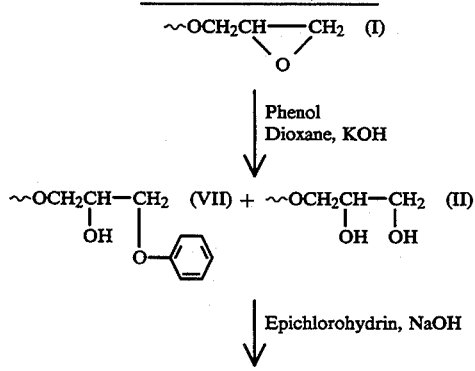

-continued
REACTION SCHEME 5

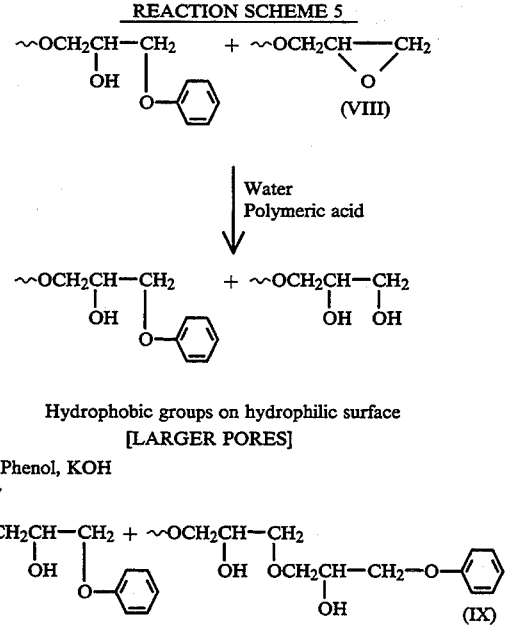

of proteins is the first separation mode used to avoid any effects of an organic solvent on the protein activity. In contrast to ion-exchange, hydrophobic separation is achieved in a decreasing gradient of the ionic salt concentration. The proteins interact with the weakly hydrophobic surface only when they are dissolved in an aqueous solution with high ionic strength ("salt-out" effect). Decrease of the salt concentration causes elution of proteins according to their hydrophobicity; this eluent is not able to displace the highly hydrophobic low molecular weight compounds held in the more hydrophobic small pores. Elution of highly hydrophobic low molecular weight compounds is achieved only with an organic solvent in a way typical of reversed phase chromatography.

A few examples, not shown in detail as Reaction Schemes, will document the flexibility of the process of the present invention. Thus, in a fashion similar to Reaction Scheme 1, an affinant (instead of an amine) reacts with the epoxide groups in small pores providing a bimodal medium wherein the separation mode is affinity interaction and the other separation mode is size exclusion. Use of the reaction with chloroacetic acid shown in Reaction Scheme 3 with the previous medium results in a new bimodal medium combining the affinity separation with ion-exchange. Finally, a reaction of the beads already modified with an affinant and then reacted with benzaldehyde leads to a bimodal separation medium providing both affinity interaction and reversed phase separation modes. Exactly the same approach, except for use of dinitroaniline or dinitrobenzylamine, may be used for the preparation of separation media combining electron donor functionality with size exclusion, ion-exchange or reversed phase. Similar combinations are available when the remaining active groups in the smaller pores react with iminodiacetic acid while the larger pores are modified in any other way. After loading the iminodiacetic groups with copper ions, the porous beads represent a bimodal medium combining ligand exchange chromatography with other modes.

Numerous combinations are obtainable using the approach shown in Reaction Scheme 4. The reactive groups located in smaller pores may react again with many different compounds presented above to produce a trimodal medium combining size exclusion, reversed phase and any other already mentioned mode.

The mobile phases, which are used in liquid chromatography, are well known in the art. Suitable mobile phases generally are water, aqueous salt solutions, organic solvents and their mixtures. Specific examples include water/acetonitrile, TRIS-HCl buffer, TRIS-HCl buffer solution/NaCl, phosphate buffer/ammonium sulfate, water/propanol, water/methanol, tetrahydrofuran, water-acetonitrile/diethylamine, hexane/methanol. The ratio of the components likely will change during the chromatographic process according to a predetermined gradient. During the elution stage of each mode of separation, the solvent may also be changed to separate slightly different molecules from each other without changing the mode of separation. For example, during a reversed-phase mode the concentration of the solvent in the eluent may be increased in a step-wise fashion to detach, during each step, a different molecule from a surface group of the separation medium to which it has attached itself. The reason this works is that different molecules have different degrees of affinity to certain surface groups. The difference in the concentration of solvent between each step will depend on the solvent being used, the molecules to be separated, the active groups in the separation medium and the duration of the eluting stage.

While the process of the present invention may be used to separate a variety a molecules from a variety of samples using a variety of combinations of separation modes, one such process is the separation of drug molecules from proteins in a blood plasma sample. This process uses a combination of size exclusion chromatography and reversed phase chromatography. Such a process uses a macroporous material such as poly[glycidyl methacrylate-ethylene dimethacrylate], as described in Reaction Scheme 1, containing both relatively large pores and relatively small pores. The large pores contain hydrophilic reactive groups and the small pores contain hydrophobic reactive groups. When a blood plasma sample (mostly water) containing large protein molecules and small drug molecules (and/or metabolites thereof) is injected into a column containing the described separation media, the large protein molecules can only penetrate the large pores which are hydrophilic. As a result, the proteins do not strongly bind to the surfaces of such pores. In contrast, the smaller drug molecules enter the small pores and bind to the hydrophobic groups therein. Thereafter, a mobile phase containing phosphate buffer solution without any organic solvent, is passed through the column. During this stage, the large protein molecules enter the relatively large pores without interaction with the hydrophilic surface of the pores and are separated in the size exclusion chromatography mode. However, the smaller drug molecules (and/or metabolites) are able to penetrate the smaller pores which have hydrophobic groups. The drug molecules because of their strong interaction with the hydrophobic groups are not eluted out of the column during the elution of the protein because of the relatively low strength of the eluent for proteins.

After the proteins are eluted out of the column, the mobile phase is changed by adding (in gradient fashion) 35 vol % acetonitrile to the phosphate buffer solution. Some drug molecules have stronger affinities than others to the hydrophobic groups. As the mobile phase changes, the drug molecules gradually move with the eluting solvent rather than remain bound to the hydrophobic groups in the pores of the separation medium. As a result, the drug molecules are separately eluted out of the column. The second separation mode is the reversed phase chromatography. Separation of a mixture of proteins and alkylbenzenes is achieved in the same column under identical conditions.

This same bimodal separation can be accomplished using ion-exchange rather than size exclusion as the first mode of separation since proteins can also easily be separated by the ion-exchange mode. The separation medium is prepared as described in Reaction Scheme 3. The surface of the relatively large pores contains attached carboxyl functionalities which provide Coulombic interactions (anion-cation interactions) with basic groups of the various proteins. The proteins adsorbed from a buffer solution with low content of salt are retained in the large pores while the electroneutral small, low molecular weight hydrophobic compounds enter even the smallest pores. They tend to interact in any aqueous buffer solution with the hydrophobic surface of the small pores rather than to remain in solution. In contrast to the previous bimodal separation, all compounds present in the sample bind to the packing, though in different sets of pores. Pumping the starting buffer solution through the column does not cause any elution of individual compounds.

The elution is initiated by increasing linearly the ionic strength of the mobile phase buffer solution through gradual addition of 1 mol/l aqueous sodium chloride. The ionic strength gradient starts with the initial buffer solution and ends with a 1:1 v/v mixture. The proteins leave the column one by one according to the strength of their interaction with the carboxylic groups of the separation medium. The species interacting most strongly are eluted at the end of the ion-exchange chromatographic mode when the ionic strength of the eluent is the highest. The salt present in the mobile phase causes not only elution of the proteins but it also increases the interaction of hydrophobic compounds already trapped in the small pores due to the "salt-out" effect. The elution of these compounds occurs when the sodium chloride solution gradient in the mobile phase is replaced with 20 vol. % acetonitrile. The organic solvent is now strong enough to break the hydrophobic interactions and initiate the motion (elution) of the small hydrophobic compounds along the column. As the mobile phase is not able to dissolve all the hydrophobic molecules completely and block all their interactions, the separated molecules still interact with the hydrophobic groups and the most hydrophobic elute slower than the less hydrophobic ones. The extent of retardation depends on the compound type and causes the separation in the reversed phase mode.

The separation path described above, i.e. first ion-exchange and then reversed phase, is very gentle toward the proteins. In contrast to the organic solvent which sometimes destroys the tertiary structure of proteins and cause their denaturation, the proteins do not lose their activity in the salt solution. However, as the ion-exchange interactions and the hydrophobic interactions are fully independent, the separation of the mixture may also start with the reversed phase separation and continue with the ion exchange mode if protein activity is not of the primary focus and need not be maintained, for example, if an analytical mode is employed where the object is to merely ascertain the presence of certain proteins. Now, the low molecular weight compounds are separated first using the buffer-organic solvent mixture as the first eluent while the proteins are separated later using an ionic strength gradient.

The process of the present invention may also be used for the separation of three classes of compounds in three different chromatographic modes. The separation medium can be prepared according to the Reaction Scheme 4 and allows separations in the size-exclusion, reversed phase and ion-exchange modes. The sample contains, for example, various proteins and low molecular weight compounds of different kinds. The first separation step involves the size exclusion mode during which all proteins with molecular or hydrodynamic volume exceeding that of the polymeric acid PA2 in water are separated according to their sizes without interaction with the separation medium. At the same time, the relatively small proteins with molecular weight in the range of from about 10,000 to about 20,000 which cannot penetrate pores smaller than those penetrable by the polymeric acid PA1 and the hydrophobic low molecular weight compounds bind to the hydrophobic benzylidene acetal groups in medium sized pores, while the charged small molecules are retained by ionic bonds in the small pores.

The chromatography is carried out as follows: the sample is injected in a dilute phosphate buffer solution mobile phase. The elution continues with the same mobile phase until all large proteins are eluted by size. Then the organic solvent gradient in the original buffer is started and the hydrophobic molecules are eluted from the medium sized pores. Finally, the charged molecules are eluted in a gradient of ionic strength. The order of the last two chromatographic modes may be changed.

The present invention will now be described with reference to the following Examples in which all parts and percents are by weight unless otherwise specified.

EXAMPLE 1

The separation medium was prepared from porous glycidyl methacrylate-ethylene dimethacrylate copolymer (60:40 v/v) beads with a diameter of 10 μm. The copolymer beads were prepared in accordance with the procedures described in U.S. Pat. No. 5,130,343 except that a mixture of cyclohexanol and dodecanol was used as proogen instead of the polymeric porogen. The original porous beads possessed a specific surface area of 114 $m^2/g$, a specific pore volume 1.1 ml/g, and pores sized to accommodate soluble low molecular weight compounds and polystyrene standards with molecular weight up to 340,000 (upper exclusion limit). The median pore size calculated from size exclusion chromatography is 13.8 nm. The original beads contain 2.7 mmol/g reactive epoxide groups used for the modification below.

The beads were modified according to Reaction Scheme 1. The beads (10 g) were suspended in 50 ml aqueous 1 wt % solution of poly(styrenesulfonic acid), molecular weight 5,000 (PSSA 5000) with very narrow molecular weight distribution. The epoxide groups located in the pores large enough to be reached by the polymeric acid catalyst were hydrolyzed for 72 hours at room temperature. The beads were filtered off and thoroughly washed on the filter with water until the filtrate was no longer acidic, then with methanol, and then dried. The hydrolysis rendered the larger pores hydrophilic as they contained diol functionalities that are appropriate for the size exclusion chromatography of proteins.

The beads were then suspended in 20 g octadecylamine and stirred slowly at 75° C. for 20 hours. 150 ml 1,4-dioxane was added and the stirring continued for another 4 hours. The beads were filtered, washed with dioxane, water, and methanol, and dried.

The aminolysis changed the epoxide groups remaining in the pores with a size smaller than that of PSSA 5,000 in water to a more hydrophobic octadecyl functionality that is effective in reversed phase chromatographic mode.

The resulting bimodal separation medium contained two different functionalities localized in pores of two different size categories: (i) hydrophilic vicinal hydroxyl groups in pores larger than the molecular size of PSSA 5,000 in water and (ii) more hydrophobic octadecyl groups in pores smaller than the molecular size of PSSA 5,000 in water. Both types of functionalities are strictly separated in selected pores as the chosen reaction route together with the control of size of the starting catalyst (chosen for its narrow polydispersity) makes any significant overlapping of functionalities impossible.

A liquid chromatography column 300 mm long and 7.8 mm in diameter was packed with 5.4 ml of separation medium comprising the modified beads in a flow of water under a constant pressure of 10 MPa.

An artificial sample (20 μl) analogous to a blood plasma comprising proteins (1% w/v) and anticonvulsant drugs (0.1% w/v) was injected in the column. The first mode of separation employed was size exclusion. During this separation mode the column was eluted with 0.1 mol/l aqueous phosphate buffer solution containing 0.15 mol/l sodium chloride at a flow rate of 0.2 ml/min. The protein molecules including thyroglobulin, human serum albumin (HSA), carbonic anhydrase, ribonuclease, as well as vitamin B12 were separated during the size exclusion chromatographic mode. After 60 minutes of eluting the proteins with buffer/sodium chloride mobile phase, the mobile phase was changed to the buffer solution only for 3 minutes, and then the mode was changed to a reversed phase mode by changing the mobile phase to a 65:35 v/v mixture of a 0.1 mol/l aqueous phosphate buffer solution and acetonitrile; the flow rate was 1 ml/min. Within less than 40 minutes the anticonvulsant drugs, phenobarbital, phenytoin, and carbamzepine, were separated.

The result of this dual mode chromatographic separation and the order of the separation are shown with the authentic chromatogram in FIG. 1.

EXAMPLE 2

The same column as prepared and used in Example 1 was used for the separation of a sample containing proteins and aromatic hydrocarbons. The new sample (20 μl) containing proteins (1.0% w/v) and aromatic hydrocarbons (0.1% w/v). The proteins were first separated in a size exclusion chromatographic mode followed by separation of the aromatic hydrocarbons (second group) in a reversed phase chromatographic mode.

The first mode of separation employed was size exclusion. During this separation mode the column was eluted with 0.1 mol/l aqueous phosphate buffer solution containing 0.15 mol/l sodium chloride at a flow rate of 0.2 ml/min. The protein molecules including thyroglobulin, human serum albumin, carbonic anhydrase, ribonuclease, as well as vitamin B12 were separated during the size exclusion chromatographic mode. After 60 minutes of eluting the proteins with the phosphate buffer/sodium chloride mobile phase, the mobile phase was changed to the buffer solution only for an additional 3 minutes. Then the mode was changed to a reversed phase mode by changing the mobile phase. The mobile phase used was a 65:35 v/v mixture of the 0.1 mol/l aqueous phosphate buffer solution and acetonitrile, the flow rate was 1 ml/min. Within less than 50 minutes the benzene, toluene, ethylbenzene, propylbenzene, butylbenzene, and amylbenzene were separated.

Figure 2:
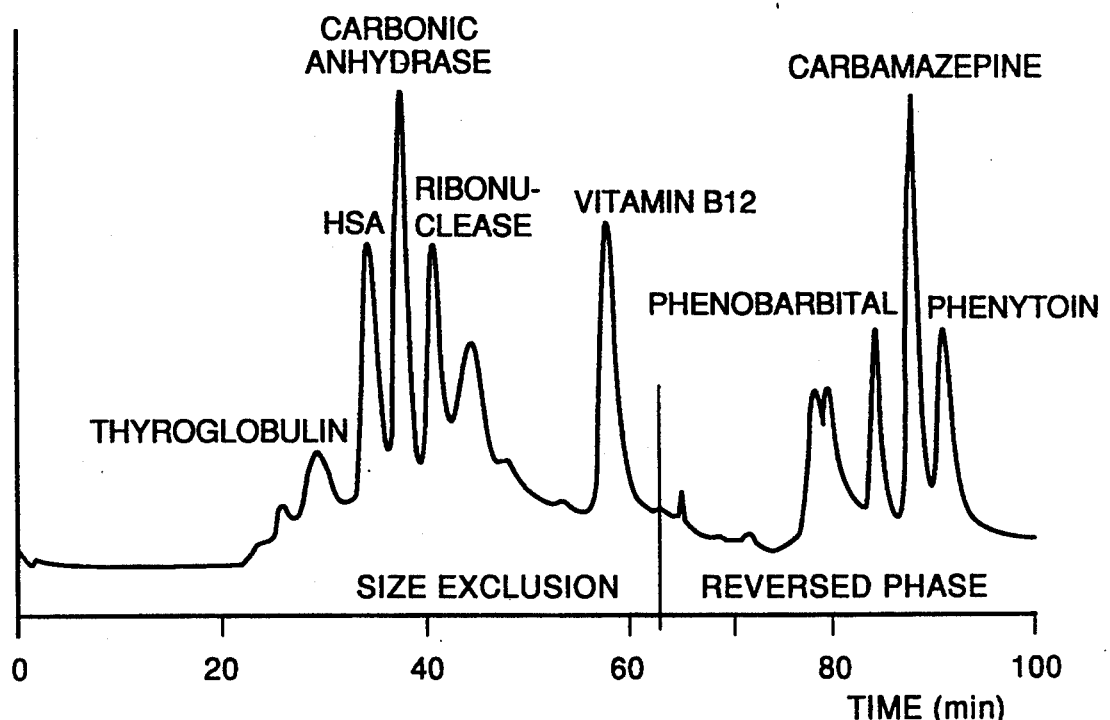

The result of this bimodal chromatographic separation and the order of the separation are shown on the authentic chromatogram in FIG. 2.

EXAMPLE 3

The polymer beads were first modified in the same way as described in Example 1. After finishing the first and second reaction steps, 1.5 g of beads containing diol and octadecyl functionality were suspended in 20 ml water, stirred at room temperature for 15 hours and filtered. The beads were transferred to a 100 ml round bottomed flask and 20 ml 50 wt % potassium hydroxide added. The mixture was stirred for 1 hour and 20 ml epichlorohydrin was added. The activation of the beads proceeded for 3 hours. The beads were filtered and washed thoroughly with dioxane, acetone and water. The product was suspended in a mixture comprising 20 ml water and 20 ml diethylamine and stirred under reflux for 6 hours. After cooling the beads were filtered, washed with water until the filtrate did not contain any amine, then with methanol and dried.

This technique produces a separation medium possessing (i) hydrophobic groups in pores smaller than the molecular size of PSSA 5,000 in water and (ii) ion-exchange groups in pores larger than the molecular size of PSSA 5,000 in water. The beads are suitable for use in reversed phase and ion-exchange bimodal separations.

A liquid chromatography column 50 mm long and 8 mm in diameter was packed with about 2.5 ml separation medium from a slurry in a flow of water under a constant pressure of 11 MPa.

An artificial sample (20 µl) comprising proteins and anticonvulsant drugs was injected in the column. The first mode of separation employed was ion-exchange. During this separation mode the column was eluted with a mixture changing its composition within 15 minutes according to a programmed gradient from 0 to 50 vol. % of 1.0 mol/l sodium chloride in 0.01 mol/l aqueous TRIS-HCl buffer solution at a flow rate of 1.0 ml/min. The protein molecules including myoglobin, Cytochrom C, bovine serum albumin (BSA), and soya bean trypsin inhibitor were separated during the ion-exchange chromatographic mode. The separation was monitored by a UV detector at a wavelength of 280 nm.

After 12 minutes of separating the proteins and 3 minutes of washing the column with the TRIS-HCl buffer only, the mode was changed to a reversed phase mode by changing the mobile phase. The mobile phase used was a 80:20 v/v mixture of the 0.1 mol/l aqueous TRIS-HCl buffer solution and acetonitrile; the flow rate was 1 ml/min. Within less than 15 minutes the anticonvulsant drugs, carbamazepine and phenytoin were separated. The separation was monitored by a UV detector at a wavelength of 254 nm.

Figure 3:
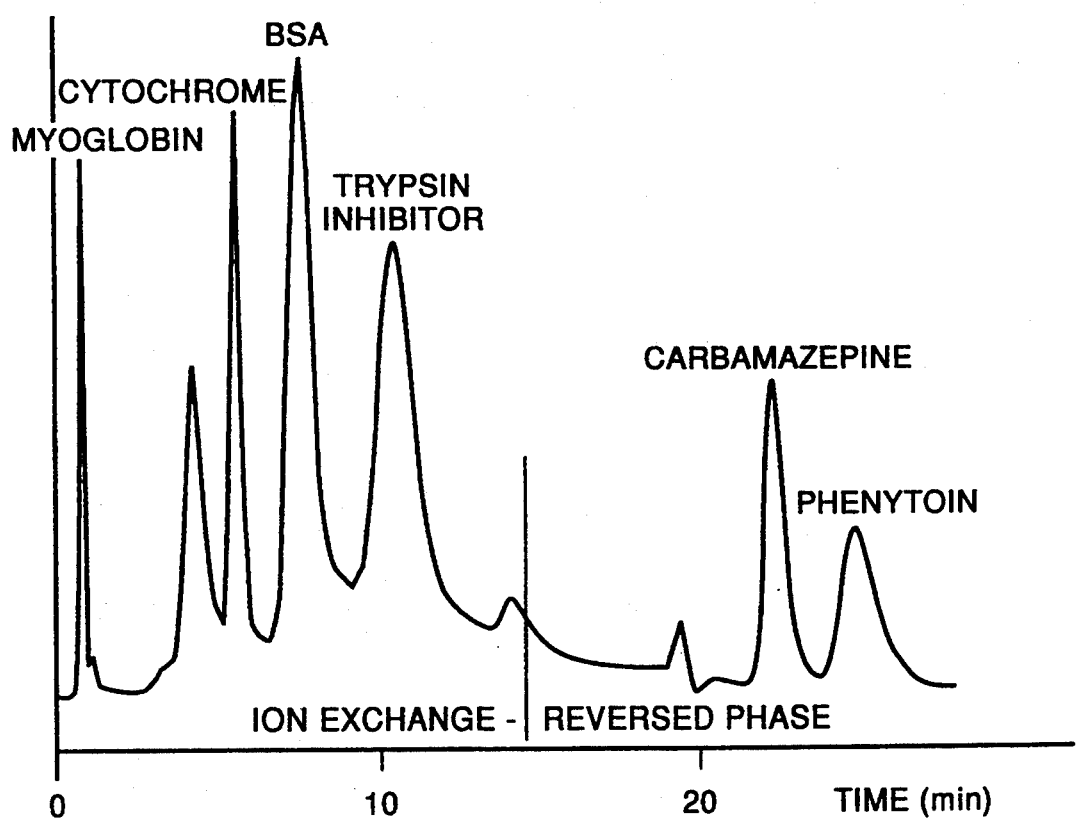

The result of this bimodal chromatographic separation and the order of the separation are shown on the authentic chromatogram of FIG. 3.

EXAMPLE 4

The beads and chromatographic column used in Example 3 was used for the separation of a sample which contained proteins and aromatic hydrocarbons. The first group of molecules (proteins) was separated using an ion-exchange mode followed by separation of the second group of compounds (aromatic hydrocarbons) using the reversed phase mode.

A sample (20 µl) comprising proteins and aromatic hydrocarbons was injected in the column. The first mode of separation employed was ion-exchange. During this separation mode the column was eluted with a mixture changing its composition within 15 minutes according to a programmed gradient from 0 to 50 vol. % of 1.0 mol/l sodium chloride in 0.01 mol/l aqueous TRIS-HCl buffer solution at a flow rate of 1.0 ml/min. The protein molecules including myoglobin, Cytochrom C, bovine serum albumin, and soya been trypsin inhibitor were separated during the ion-exchange chromatographic mode. The separation was monitored by a UV detector at a wavelength of 280 nm.

After 15 minutes of separating the proteins and 3 minutes washing the column with the buffer only, the mode was changed to a reversed phase mode by changing the mobile phase. The mobile phase used was a 80:20 v/v mixture of the 0.1 mol/l aqueous TRIS-HCl buffer solution and acetonitrile, the flow rate was 1 ml/min. Within less than 15 minutes, the aromatic hydrocarbons, i.e. toluene, ethylbenzene and propylbenzene, were separated. The separation was monitored by a UV detector at a wavelength of 254 nm.

Figure 4:
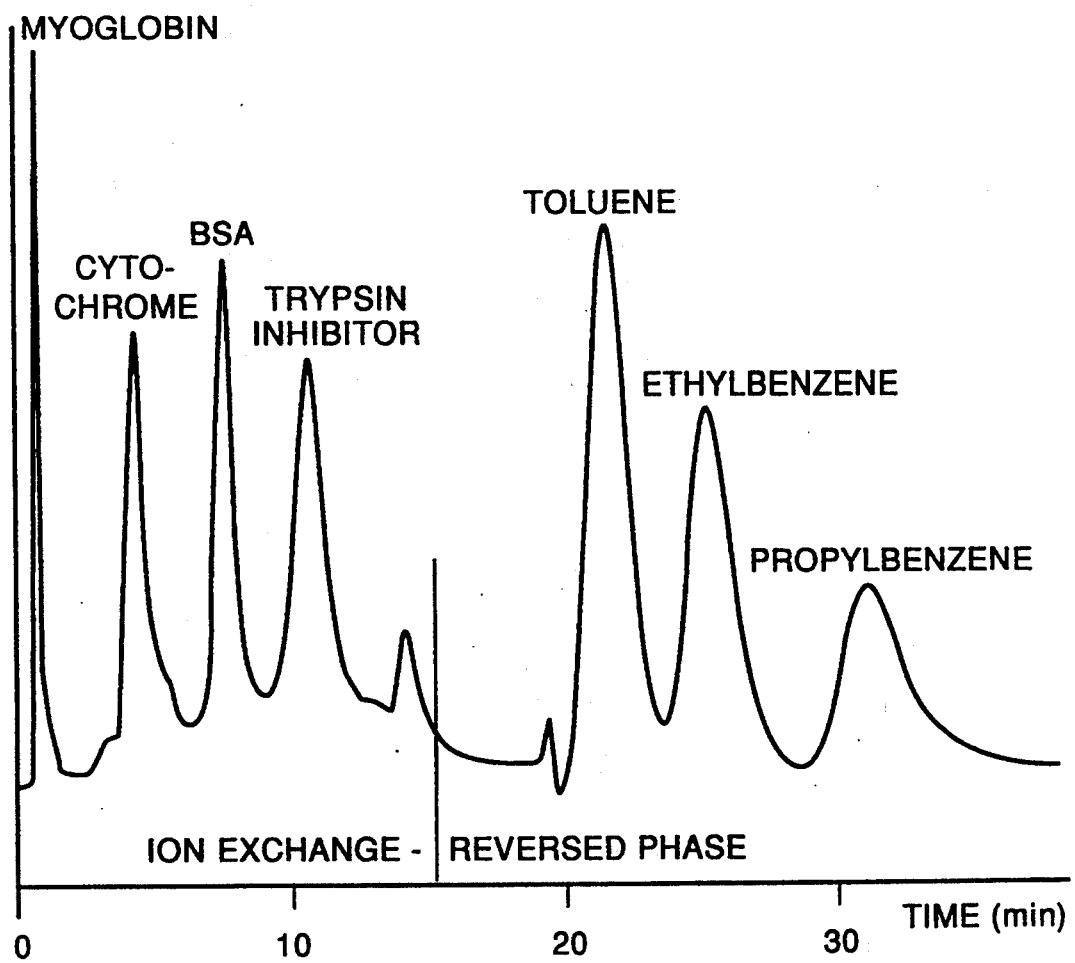

The result of this bimodal chromatographic separation and the order of the separation are shown on the authentic chromatogram in FIG. 4.

EXAMPLE 5

The same column as used in the Examples 3 and 4 was used for the separation of a further sample containing proteins and aromatic hydrocarbons. The hydrocarbons were separated in reversed phase mode followed by separation of the proteins in an ion-exchange mode.

A sample comprising proteins and aromatic hydrocarbons was injected in the column. The first mode of separation employed was reversed phase. The mobile phase used was a 80:20 v/v mixture of the 0.1 mol/l aqueous TRIS-HCl buffer solution and acetonitrile, the flow rate was 1 ml/min. Within less than 15 minutes, the aromatic hydrocarbons, toluene, ethylbenzene and propylbenzene were separated. The separation was monitored by an UV detector at a wavelength of 254 nm.

After 20 minutes of separating the hydrocarbons and 4 minutes washing the column with the TRIS-HCl buffer, the mode was changed to ion-exchange. During this separation mode the column was eluted with a mixture changing its composition within 15 minutes according to a programmed gradient from 0 to 50 vol % of 1.0 mol/l sodium chloride in 0.01 mol/l aqueous TRIS-CHl buffer solution at a flow rate of 1.0 ml/min. The protein molecules including myoglobin, Cytochrom C, bovine serum albumin (BSA), and soya been trypsin inhibitor were separated during the ion-exchange chromatographic mode. The separation was detected by an UV detector at a wavelength of 280 nm.

Figure 5:
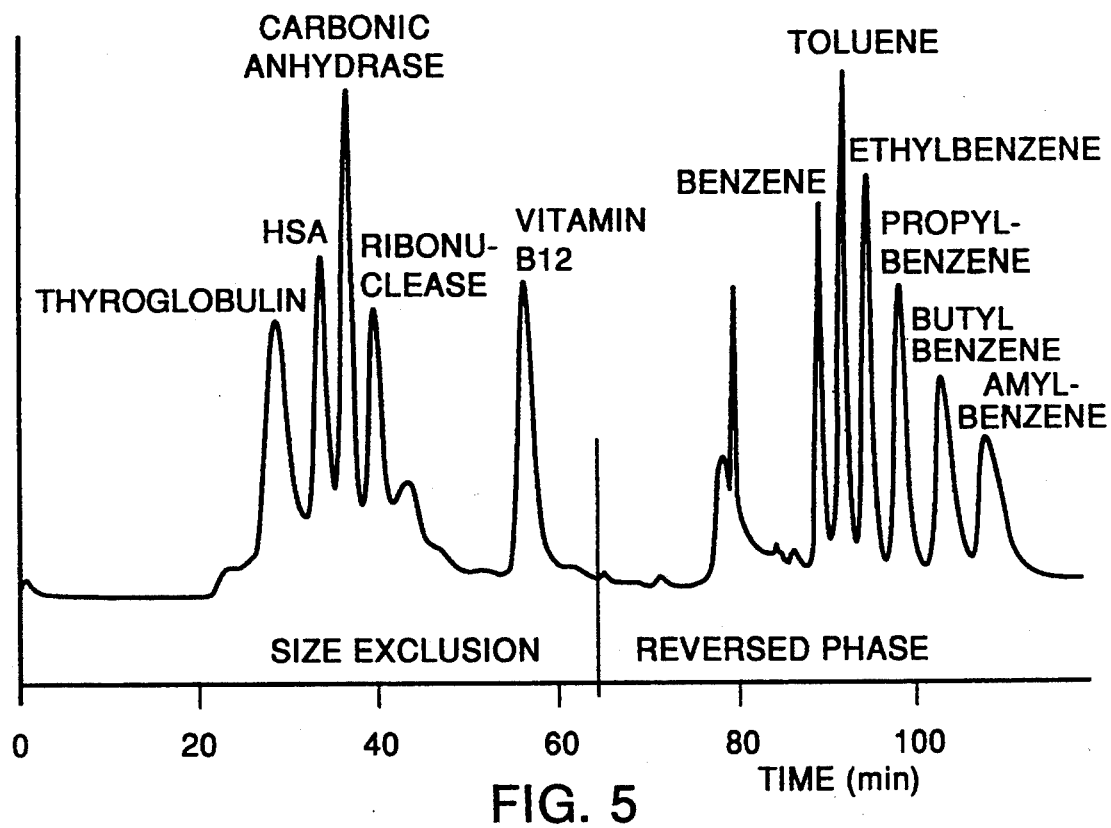

The result of this bimodal chromatographic separation and the order of the separation are shown on the chromatogram in FIG. 5.

EXAMPLE 6

Preparation of the separation medium for this Example followed Reaction Scheme 5.

The same initial porous polymer beads as used in Example 1 prepared of a glycidyl methacrylate-ethylene dimethacrylate copolymer (1.6 g) were suspended in 60 ml dioxane solution containing 0.01 g potassium hydroxide and 1 g phenol. The mixture was stirred under reflux for 2 hours. The beads were filtered, washed consecutively with dioxane, acetone, water, and acetone again and dried.

For a second reaction step, the beads were dispersed in 20 ml water and slowly stirred for 15 hours. After filtration, the wet beads were redispersed in 20 ml 50 wt. % aqueous potassium hydroxide, left to equilibrate for 1 hour, and the remaining liquid filtered off. A mixture of 20 ml water and 20 ml epichlorohydrin was added to the solid and the whole was mixed at room temperature for 3 hours. The modified beads were separated by filtration, washed with dioxane, acetone, water and acetone.

In a third step the beads were suspended in 10 ml aqueous 1 wt. % solution of poly(styrenesulfonic acid), molecular weight 5,000 with narrow molecular weight distribution. Hydrolysis of epoxide groups placed in pores of a size large enough to accommodate the polymeric acid catalyst was continued for 72 hours at room temperature. The beads were filtered off and thoroughly washed on the filter with water until the filtrate was neutral, then with methanol and dried. The hydrolysis renders the pores larger than the molecular size of PSSA 5,000 in water hydrophilic as they now contain the diol functionalities together with phenyl residues that are appropriate for hydrophobic interaction chromatography.

The last reaction step consists of the reaction of the epoxide reactive groups, attached in step 2 above and localized in the smaller pores, with phenol to increase the hydrophobicity of the surface. Beads resulting from step 3 above were admixed to a melt of 8 g phenol and 0.01 g potassium hydroxide and stirred at 70°–80° C. for 6 hours. The mixture was cooled down and diluted with 50 ml dioxane. An extensive washing with water and methanol and drying produced a separation medium suitable for a bimodal separation in hydrophobic interaction and reversed phase chromatographic modes.

The separation medium (5 ml) was water slurry packed in a stainless steel column 100 mm long and 8 mm in diameter. The packed column was used for separation of a sample containing proteins and aromatic hydrocarbons. The first group of molecules was separated using the hydrophobic interaction mode followed by separation of the second group of compounds using the reversed phase mode.

A sample (20 μl) comprising proteins and aromatic hydrocarbons was injected in the column. The first mode of separation employed was hydrophobic interaction. During this separation mode the column was eluted with a mixture whose composition changed in the course of 15 minutes according to a programmed gradient from 1.7 mol/l ammonium sulfate in 0.02 mol/l aqueous phosphate buffer solution (pH 7) to the buffer solution only at a flow rate of 1 ml/min. The protein molecules including Cytochrom C, ribonuclease, conalbumin, lysozyme and soya been trypsin inhibitor were separated during the hydrophobic interaction chromatographic mode. The separation was monitored by a UV detector at a wavelength of 280 nm.

Figure 6:
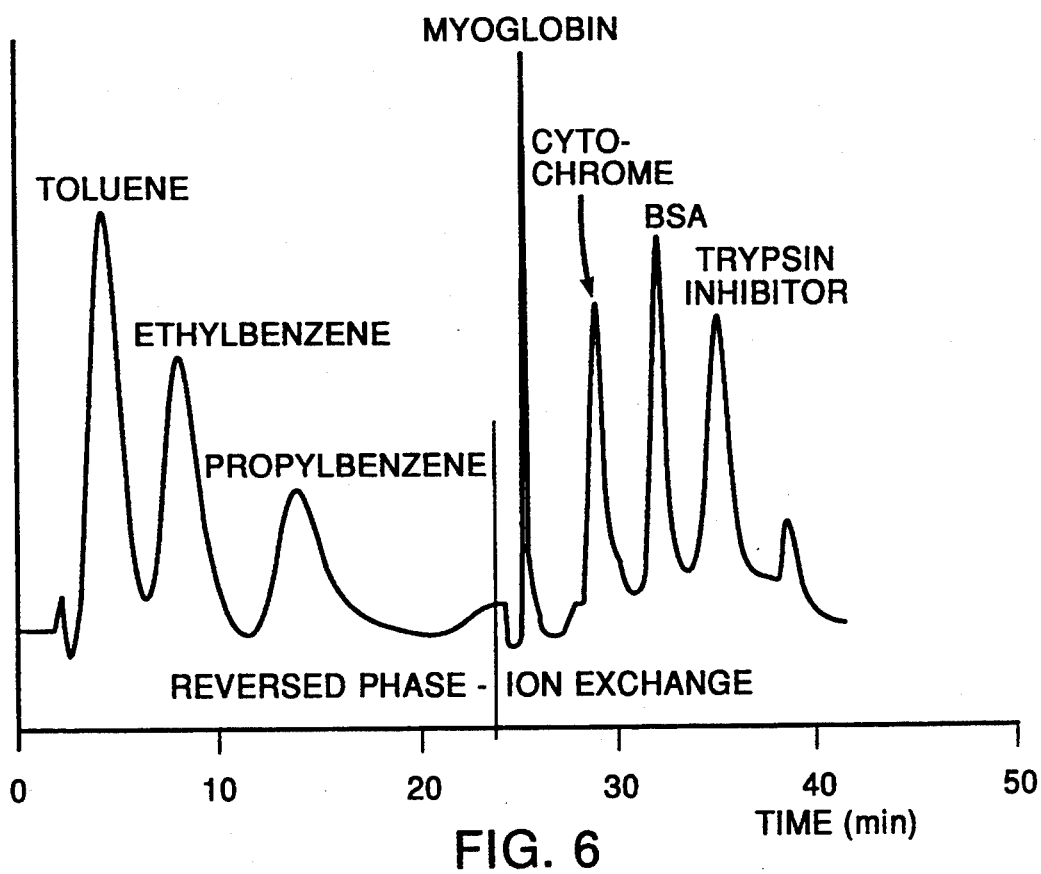
Figure 8:
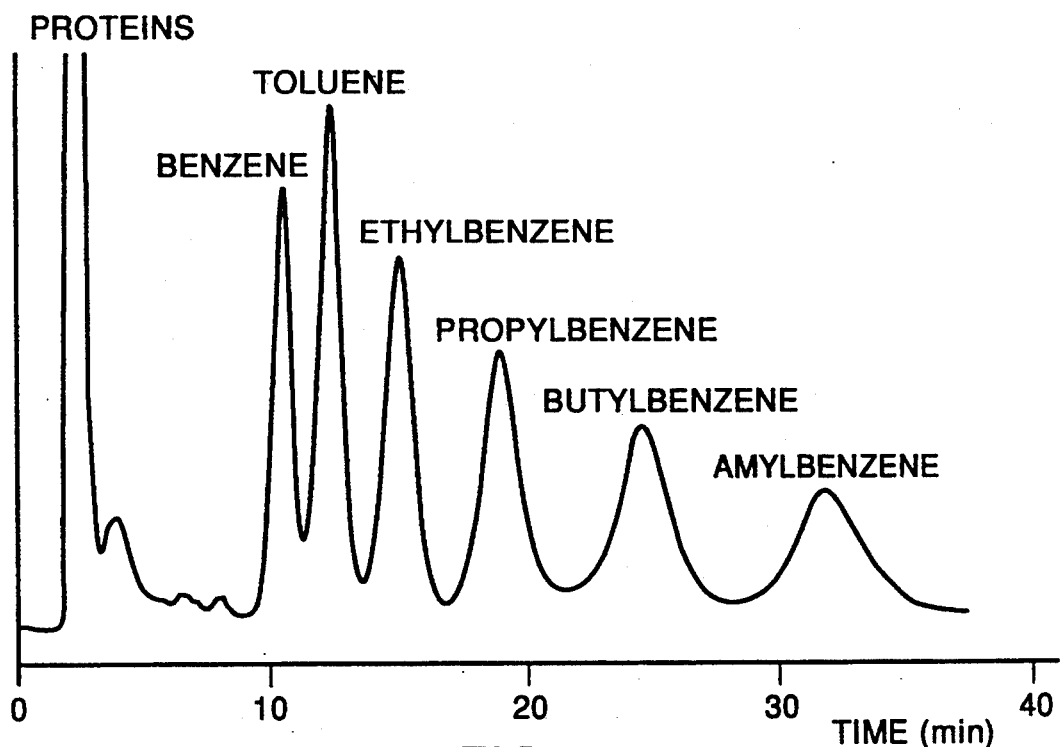

After 15 minutes of separating the proteins followed by 7 minutes of washing the column with the buffer only, the mode was changed to a reversed phase mode. The mobile phase used was 65:35 v/v mixture of 0.02 mol/l aqueous phosphate buffer solution and acetonitrile, the flow rate was 1 ml/min. Within less than 40 minutes, the aromatic hydrocarbons, toluene, ethylbenzene, propylbenzene and amylbenzene were separated. The separation was monitored by an UV detector at a wavelength of 254 nm. The results of the bimodal separation are shown in FIG. 6.

Figure 7:
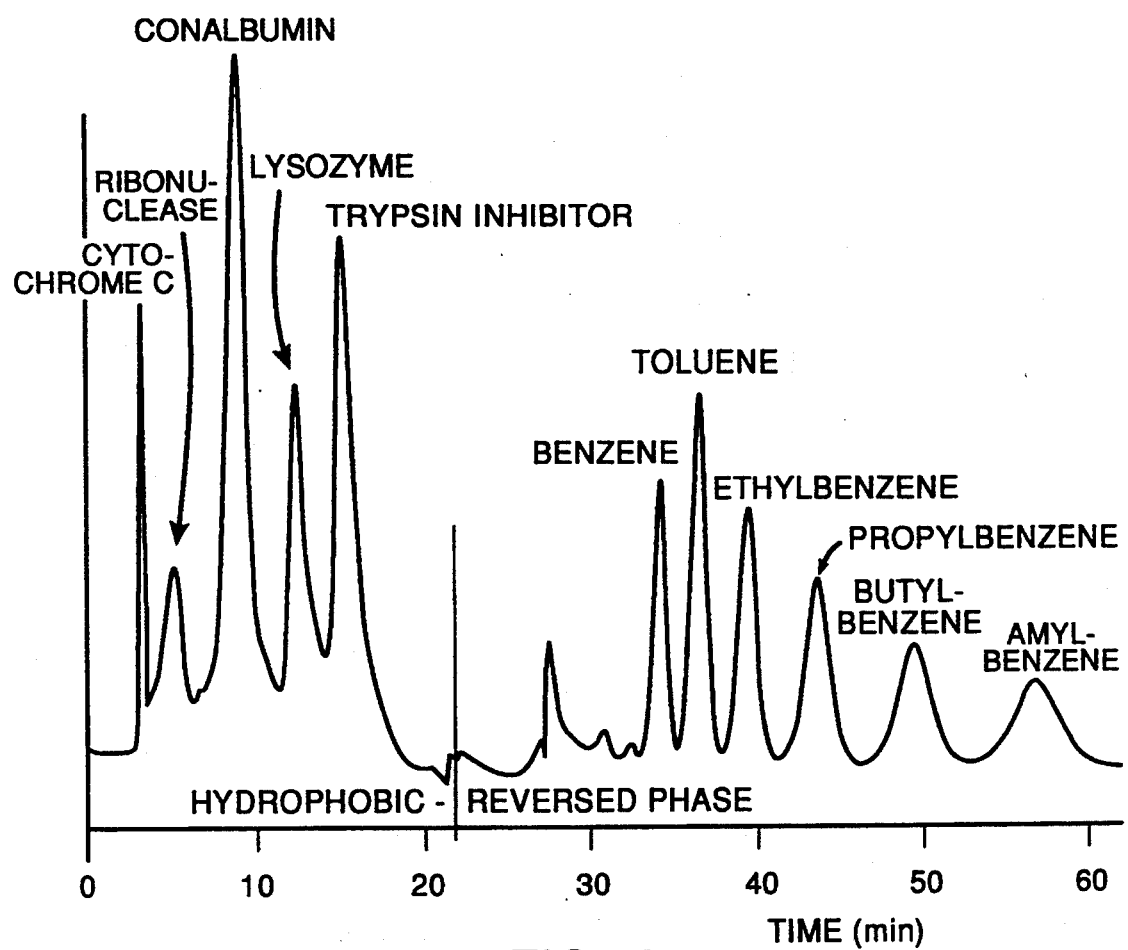

Separation of the same sample containing proteins and hydrocarbons was attempted using only the reversed phase mode while leaving out the hydrophobic interaction mode. The separation should only be successful if the proteins had access to highly hydrophobic surface. An attempt at separating the mixture was carried out in a mobile phase containing 35% acetonitrile in the phosphate buffer. FIG. 7 clearly indicates that only one peak attributed to the proteins was produced and thus that they were all eluted together without any separation thereof, while the separation of the aromatic hydrocarbons did not change and was satisfactory.

EXAMPLE 7

The same separation medium packed in the same column as used in Example 6 was used for separation of a sample containing proteins and drugs. The proteins were separated in hydrophobic interaction mode first, followed by separation of drugs in a reversed phase mode.

A sample (20 μl) comprising proteins (1% w/v) and anticonvulsant drugs (0.1% w/v) was injected in the column. The first mode of separation employed was hydrophobic interaction. During this separation mode the column was eluted with a mobile phase changing its composition within 15 minutes according to a programmed gradient from 1.7 mol/l ammonium sulfate in 0.02 mol/l aqueous phosphate buffer solution (pH 7) to the buffer solution only at a flow rate of 1 ml/min. The protein molecules including Cytochrom C, ribonuclease conalbumin, lysozyme and soya bean trypsin inhibitor were separated during the hydrophobic interaction chromatographic mode. The separation was monitored by a UV detector at a wavelength of 280 nm.

Figure 9:
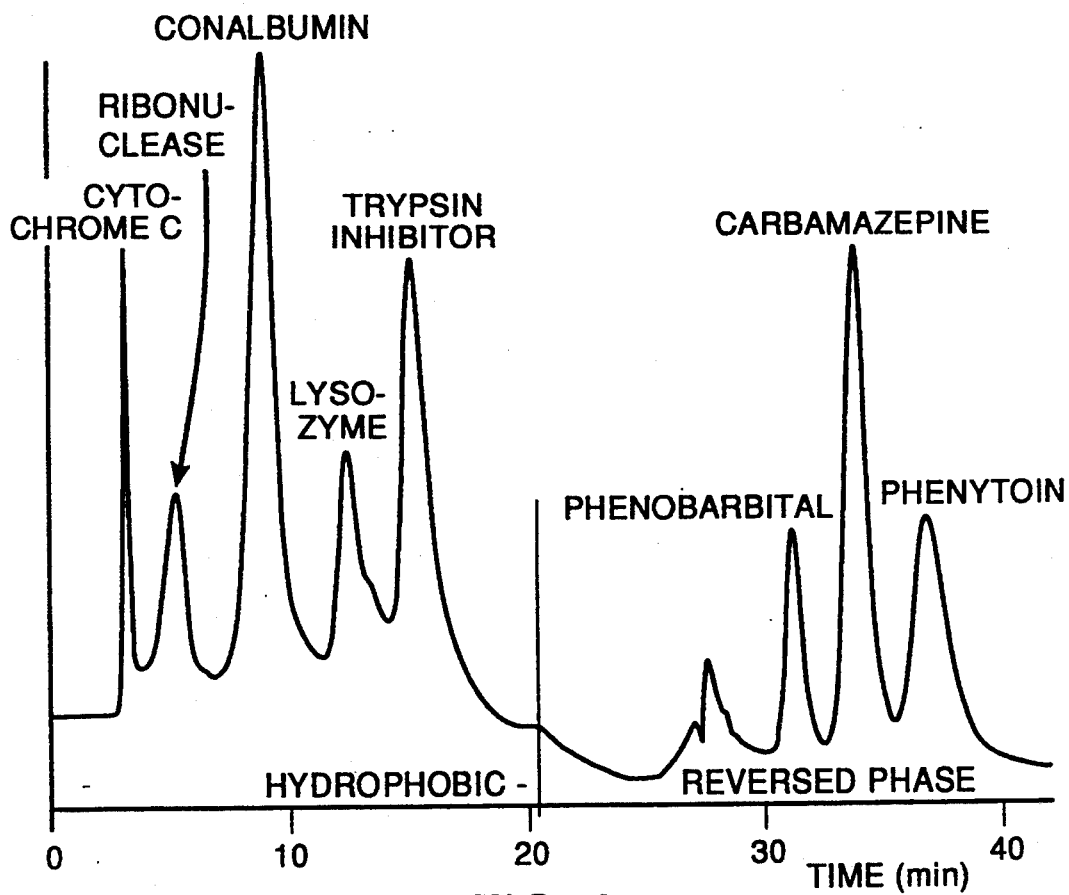

After 15 minutes of separating the proteins and 6 minutes of washing the column with the buffer only, the mode was changed to a reversed phase mode simply by changing the composition of the mobile phase. The mobile phase used was a 63:35 v/v mixture of the 0.02 mol/l aqueous phosphate buffer solution and acetonitrile, the flow rate was 1 ml/min. Within less than 20 minutes, the aromatic drugs phenobarbital, carbazepamine and phenytoin were separated. The separation was monitored by a UV detector at a wavelength of 254 nm. The bimodal separation is shown in FIG. 9.

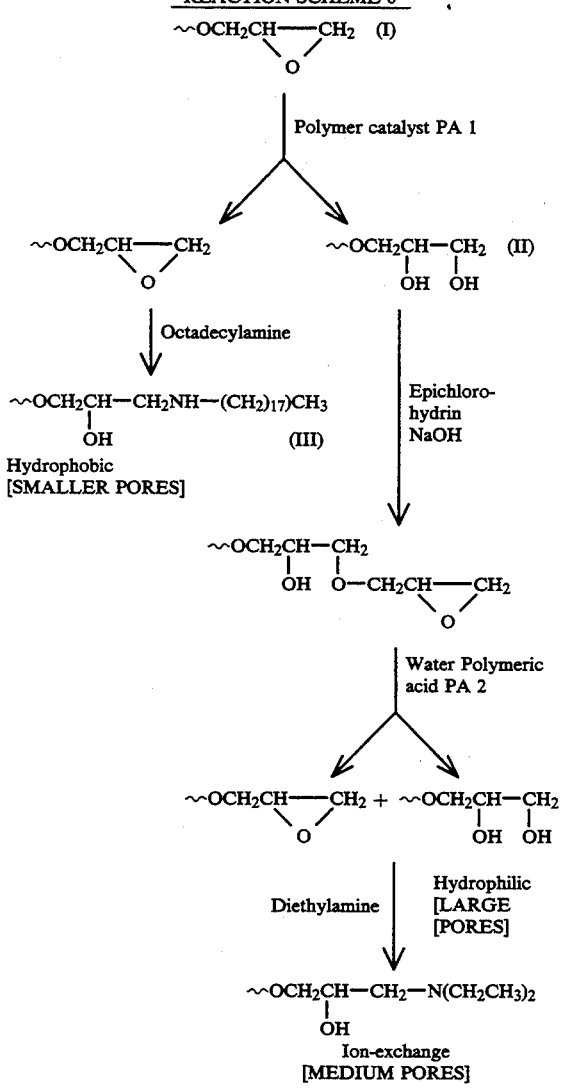

REACTION SCHEME 6

EXAMPLE 8

A trimodal separation medium was prepared from porous glycidyl methacrylate-ethylene dimethacrylate copolymer (60:40 v/v) beads with a diameter of 10 μm. The beads were modified according to Reaction Scheme 6.

The beads (8.3 g) were suspended in 50 ml aqueous 1 wt. % solution of poly(styrenesulfonic acid), molecular weight 5,000 with very narrow molecular weight distribution. The epoxide groups located within pores larger than the molecular size of the polymeric acid catalyst in water were left to hydrolyze for 72 hours at room temperature. The beads were filtered off and thoroughly washed on the filter with water until neutral, then with methanol, and dried. The hydrolysis renders the larger pores more hydrophilic as they now contain diol functionalities. In the pores smaller than the size of PSSA 5,000 in water remain 0.4 mmol/g of unreacted epoxide groups.

The beads were then suspended in 20 g octadecylamine and stirred slowly at 75° C. for 20 hours. 1,4-Dioxane (150 ml) was added and the stirring continued for another 4 hours. The beads were filtered, washed with dioxane, water and methanol, and dried. The aminolysis changed the epoxide groups remaining in the smaller pores to a hydrophobic octadecyl functionality effective in reversed phase chromatographic mode. The beads no longer contained any epoxide groups after this treatment.

For the third reaction step, the beads were dispersed in 100 ml water and slowly stirred for 15 hours. After removal of water on a filter, the wet beads were redispersed in 100 ml 50 wt. % aqueous potassium hydroxide, left to equilibrate for 1 hour and the remaining liquid was removed on a filter. A mixture of 50 ml water and 50 ml epichlorohydrin was added to the solid and mixed at room temperature for 15 hours. The product was separated by filtration, washed with dioxane, acetone, water and acetone. The reactivated beads now contained on 0.7 mmol/g of epoxide groups as determined by titration.

The beads were suspended in 50 ml aqueous 1 wt. % solution of poly(styrenesulfonic acid), molecular weight 47,000 with very narrow molecular weight distribution. Hydrolysis of epoxide groups placed in pores larger than size of poly(styrenesulfonic acid) MW 47,000 in water were hydrolyzed for 72 hours at room temperature. The beads were filtered off and washed on filter with water until neutral, then with methanol, and dried. The hydrolysis renders the pores larger than the size of the polymeric catalyst in water hydrophilic as they now contain diol functionalities. At this stage an analysis of the beads showed that they still contained 0.28 mmol of epoxide groups per gram of beads.

The last reaction step consists of the reaction of the additionally attached epoxide reactive groups localized in the smaller pores with diethylamine. The beads were suspended in a mixture comprising 50 ml water and 50 ml diethylamine and stirred under reflux for 6 hours. After cooling, the beads were filtered, washed with water until the filtrate did not contain any amine, then with methanol and dried.

This technique produces a separation medium possessing (i) hydrophobic groups in pores smaller than the molecular size of PSSA 5,000 in water, (ii) ion-exchange groups in pores larger than the molecular size of PSSA 5,000 in water but smaller than the molecular size of PSA 47,000 in water, and (iii) hydrophilic groups in pores larger than the molecular size of PSSA 47,000 in water. The resulting beads are suitable for use in size-exclusion, reversed phase, and ion-exchange trimodal separation.

A liquid chromatography column 300 mm long and 7.8 mm in diameter was packed with 5.4 ml trimodal separation medium comprising the modified beads in a flow of water under a constant pressure of 10 MPa.

A sample (20 μl) comprising proteins and aromatic hydrocarbons was injected in the column. The first mode of separation employed was size exclusion. The column was eluted with 0.1 mol/l aqueous phosphate buffer solution containing 0.15 mol/l sodium chloride at a flow rate 1 ml/min. The protein molecules including thyroglobulin and myoglobin were separated during the size-exclusion chromatographic mode. After 12 minutes of eluting the first proteins, the mode was changed to an ion-exchange. During this separation mode the column was eluted at a flow rate of 1.0 ml/min with a mixture changing its composition according to a programmed gradient from 0 to 50 vol.% of 1.0 mol/l sodium chloride in 0.01 mol/l aqueous TRIS-HCl buffer solution within 15 minutes. The protein molecules with similar molecular weight including Cytochrom C, bovine serum albumin, and soya been trypsin inhibitor were separated during the ion-exchange chromatographic mode. The separation was monitored by a UV detector at a wavelength of 280 nm.

After 15 minutes of separating the proteins the mode was changed to a reversed phase mode. The mobile phase used was a 80:20 v/v/mixture of the 0.1 mol/l aqueous TRIS-HCl buffer solution and acetonitrile, the flow rate was 1 ml/min. Within about 15 minutes, the aromatic hydrocarbons, toluene, ethylbenzene and propylbenzene were separated. The separation was monitored by a UV detector at a wavelength of 254 nm.

Figure 10:
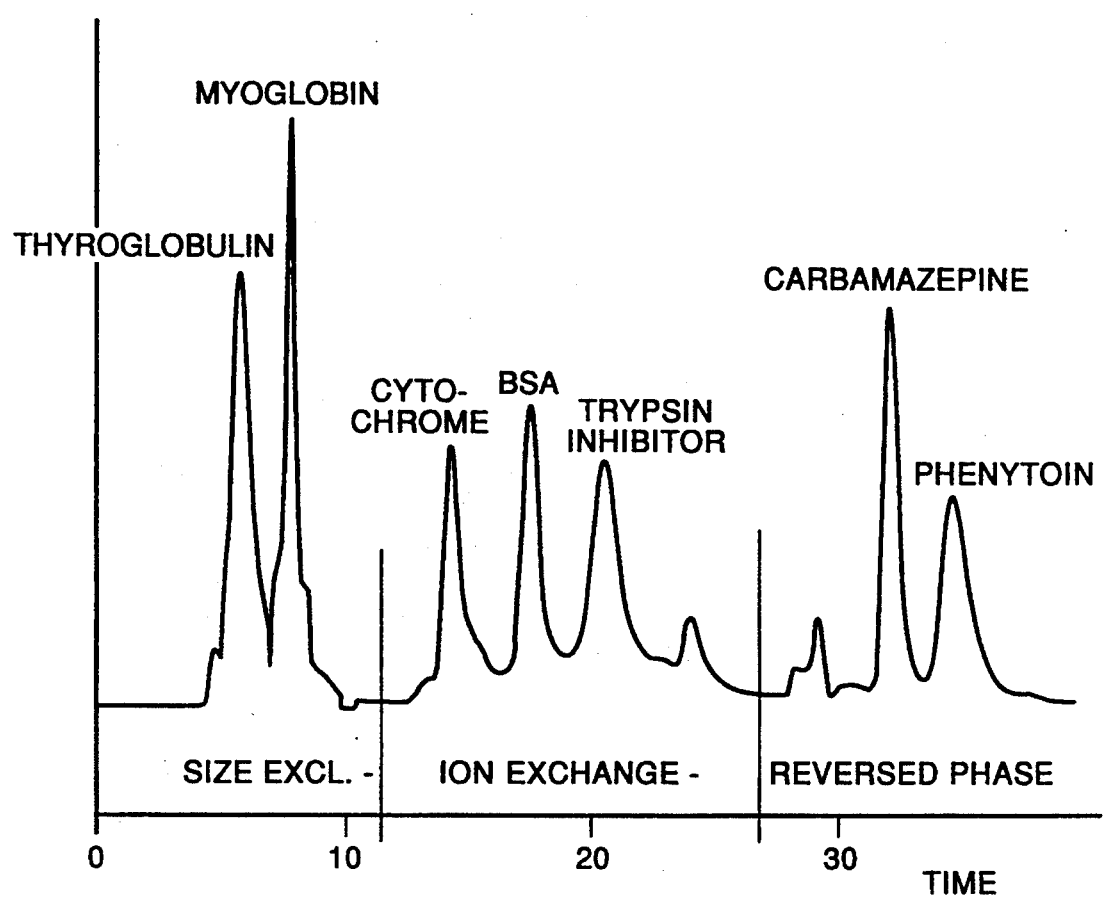

The result of this trimodal chromatographic separation and the order of the separation are shown on the authentic chromatogram of FIG. 10.

What is claimed:

1. A multimodal separation medium for use in liquid chromatography comprising a porous separation medium having at least two different pore size ranges with each pore size range containing a different surface group, having a different functionality compared to the surface groups in the other pore size range, said porous separation medium being capable of separating molecules in a sample added to a chromatography column containing said separation medium during different modes of separation which are carried out in a consecutive fashion using a single separation medium.

2. A multimodal separation medium for use in chromatography comprising a porous separation medium having at least two ranges of pore size, with each range of pore sizes having surface groups of a chemical composition different from that of other pore size ranges.

3. The separation medium of claim 2, wherein the porous material has relatively large pores, medium size pores, and relatively small pores, with the relatively large pores one type of surface groups disposed therein, medium pores have another type of surface groups, and the relatively small pores have again another surface groups disposed therein with each type of surface groups having a different functionality compared to the other types.

4. The separation medium of claim 2, wherein the porous material is a macroporous material.

5. The separation medium of claim 2, wherein the porous material is a polymer of any of glycidyl methacrylate or acrylate; 2-hydroxyethyl methacrylate or acrylate; allyl methacrylate or acrylate; chloromethylstyrene; 4-tert-butoxycarbonyloxystyrene; vinylacetate; vinylacetals; vinyl alcohol, vinylbenzyl alcohol or vinyl phenol and esters or ethers ,thereof; 4-nitrophenyl acrylate; 2,4,5-trichlorophenyl acrylate; acryloyl succinimide; maleic acid; vinylbenzaldehyde, acrolein, or methacrolein or acetal, imine, oxime, or hydrazone derivatives thereof; crosslinked with any of divinylbenzene; ethylene dimethacrylate or acrylate; diethylene glycol methacrylate or acrylate; divinylpyridine; bis-N-vinyl-2-pyrrolidone; N, N-methylene-bis-acrylamide; or trimethylolpropane trimethacrylate.

6. The separation medium of claim 2, wherein the porous material is a polymer or copolymer prepared from monomers selected from any of styrene, acrylic acid and its esters, methacrylic acid and its esters, vinylpyridine, maleate, vinylester, vinyl ether, and vinylalcohol derivatives, crosslinked with divinylbenzene, ethylene dimethacrylate or diacrylate, diethylene glycol dimethacrylate or diacrylate, divinylpyridine, bis-N-vinyl-2-pyrrolidone, N,N-methylene-bisacrylamide or bismethacrylamide, or trimethylolpropane trimethacrylate.

7. The separation medium of claim 2, wherein the porous material is an inorganic oxide.

8. The separation medium of claim 7, wherein the inorganic oxide is selected from any of silica, titania, zirconia, alumina, magnesia or glass.

9. The separation medium of claim 2, wherein the porous material is a bonded material comprising the reaction product of the inorganic oxide and a silylation agent.

10. The separation medium of claim 2, wherein the porous material is a natural polysaccharide porous polymer.

11. The separation medium of claim 10, wherein the porous polysaccharide polymer is selected from any of cellulose, chitin, agarose, dextran, mannan or guar.

12. The separation medium of claim 2, wherein the separation medium possesses at least two different functionalities.

13. The separation medium of claim 12, wherein the functionalities are ion-exchange and hydrophobic.

14. The separation medium of claim 12, wherein the functionalities are hydrophobic and hydrophilic.

15. The separation medium of claim 12, wherein the functionalities are hydrophilic and ion-exchange.

16. The separation medium of claim 2, wherein the separation medium possesses two different polarities.

17. The separation medium of claim 2, wherein the separation medium possesses three different functionalities.

18. The separation medium of claim 17, wherein the functionalities are hydrophilic, ion-exchange, and hydrophobic.

19. The separation medium of claim 2, wherein one pore size range contains 1,2-diol groups and a second pore size range contains acetal groups.

20. The separation medium of claim 2 wherein one pore size range contains dialkylamino groups and the second pore size range contains diol groups.

21. The separation medium of claim 2, wherein one pore size range contains diethylamino groups and a second pore size range contains 1,2-diol groups.

22. The separation medium of claim 2, wherein one pore size range contains octadecyl groups and a second pore size range contains 1,2-diol groups.

23. The separation medium of claim 2, wherein one pore size range contains acetal groups and a second pore size range contains carboxylic groups.

24. The separation medium of claim 2, wherein one pore size range contains phenyl groups and a second pore size range contains phenyl and 1,2-diol groups.

25. The separation medium of claim 2, wherein one pore size range contains octadecyl groups, second pore size range contains diethylamino groups and a third-pore size range contains 1,2-diol groups.

26. The separation medium of claim 2, wherein one pore size range contains diethylamino groups, second pore size range contains acetal groups and a third pore size range contains 1,2-diol groups.

27. The separation medium of claim 2, wherein one pore size range contains alcohol groups and a second pore size range contains ester groups.

28. The separation medium of claim 2, wherein one pore size range contains alcohol groups and a second pore size range contains carbonate groups.

29. The separation medium of claim 2, wherein one pore size range contains ester groups and a second pore size range contains amide groups.

30. The separation medium of claim 2, wherein one pore size range contains cyano groups and a second pore size range contains amine groups.

* * * * *